United States Patent
Czech et al.

(10) Patent No.: US 6,653,088 B1
(45) Date of Patent: Nov. 25, 2003

(54) INTERACTION TEST FOR THE INVESTIGATION OF INHIBITORY MOLECULES OF THE INTERACTION BETWEEN A PRESENILIN AND THE β-AMYLOID PEPTIDE

(75) Inventors: Christian Czech, Grenzach-Wyhlen (FR); Luc Mercken, Saint Maur (FR); Laurent Pradier, Verrieres (FR); Soline Reboul-Becquart, Montrouge (FR)

(73) Assignee: Aventis Pharma S.A., Antony (FR)

(*) Notice: Subject to any disclaimer, the term of this patent is extended or adjusted under 35 U.S.C. 154(b) by 0 days.

(21) Appl. No.: 09/415,099

(22) Filed: Oct. 8, 1999

Related U.S. Application Data

(63) Continuation of application No. PCT/FR98/02278, filed on Oct. 23, 1998.
(60) Provisional application No. 60/103,553, filed on Oct. 8, 1998.

(30) Foreign Application Priority Data

Oct. 24, 1997 (FR) ............................................. 97 13384

(51) Int. Cl.[7] .......................... C12Q 1/00; G01N 33/53; C07K 2/00; C07K 14/00
(52) U.S. Cl. ............................. 435/7.1; 435/4; 435/7.5; 435/7.8; 530/300; 530/350
(58) Field of Search ............................... 435/4, 7.1, 7.5, 435/7.8, 7.9, 7.92, 69.1; 530/300, 350

(56) References Cited

U.S. PATENT DOCUMENTS

| 5,527,684 A | * | 6/1996 | Mabile et al. ............... 435/7.1 |
| 6,040,174 A | | 3/2000 | Imler et al. | |

FOREIGN PATENT DOCUMENTS

| EP | 185 573 | 5/1992 |
| WO | WO 91/18088 | 11/1991 |
| WO | WO 94/12649 | 6/1994 |
| WO | WO 97/27296 | 6/1994 |
| WO | WO 94/26914 | 11/1994 |
| WO | WO 94/28152 | 12/1994 |
| WO | WO 94/28938 | 12/1994 |
| WO | WO 95/02697 | 1/1995 |

OTHER PUBLICATIONS

US 5,891,715, 4/1999, Haddada et al. (withdrawn)
Grunberg et al. Truncated presenilin 2 derived from differentially spliced mRNAs does not affect the ratio of amyloid beta–peptide 1–42/1–40. Neuroreport 9: 3293–3299, 1998.*
Higaki et al. Inhibition of beta–amyloid formation identifies proteolytic precursors and subcellular site of catabolism. Neuron 14: 651–659, 1995.*
Krull et al. Labeling reactions applicable to chromatography and electrophoresis of minute amounts of proteins. J Chromatography B 699: 173–208, 1997.*
Tomita et al. Molecular dissection of domains in mutant presenilin 2 that mediate overproduction of amyloidogenic forms of amyloid beta peptides. J Biol Chem 273(33): 21553–21160, 1998.*
Waragai et al. Presenilin 1 binds to amyloid precursor protein directly. Biochem Biophys Res Comm 239: 480–482, 1997.*
Weidemann et al. Identification, biogenesis, and localization of precursors of Alzheimer's disease A4 amyloid protein. Cell 57: 115–126, 1989.*
Thinakaran, et al. Stable Association of Presenilin Derivatives and Absence of Presenilin Interactions with APP. Neurobiology of Disease 4:438–453 (1998).
Weidemann et al., Formation of stable complexes between two Alzheimer's disease gene products: Presenilin–2 and B–amyloid precursor protein, Nature Medicine 3(3), 328–332 (1997).
Blanchard et al., Immunohistochemical analysis of presenilin 2 expression in the mouse brain: distribution pattern and co–localization with presenilin 1 protein, Brain Research 758, 209–217 (1997).
Hardy, Amyloid, the presenilins and Alzheimer's disease, TINS 20(4), 154–159 (1997).
Xia et al., Interaction between amyloid precursor protein and presenilins in mammalian cells: Implications for the pathogenesis of Alzheimer disease, Proc. Natl. Acad. Sci. 94, 8208–8213 (1997).
Le Gal La Salle et al., An Adenovirus Vector for Gene Transfer into Neurons and Gila in the Brain, Science 259, 988–990 (1993).
Levrero et al., Defective and nondefective adenovirus vectors for expressing foreign genes in vitro and in vivo, Gene 195–202 (1991).
Beard et al., Transcription Mapping of Mouse Adenovirus Type 1 Early Region 3, Virology 175, 81–90 (1990).
Graham et al., Characteristics of a Human Cell Line Transformed by DNA from Human Adenovirus Type 5, J. Gen. Virol. 36, 59–72 (1977).
Graham, Covalently closed circles of human adenovirus DNA are infectious, The EMBO Journal 3(12), 2917–2922 (1984).
Dyrks et al., Generation of BA4 from the amyloid protein precursor and fragments thereof, FEBS 335(1), 89–93 (1993).

(List continued on next page.)

*Primary Examiner*—Elizabeth Kemmerer
*Assistant Examiner*—Bridget E. Bunner
(74) *Attorney, Agent, or Firm*—William C. Coppola

(57) ABSTRACT

Provided herein are novel peptide and nucleotide sequences, their pharmaceutical use, as well as novel polypeptides capable of inhibiting at least partially the interaction between presenilin 1 or presenilin 2 and the β-amyloid peptide precursor or a β-amyloid peptide; also provided are in vitro tests and methods for detecting molecules and in particular, molecules capable of inhibiting said interaction.

6 Claims, 21 Drawing Sheets

OTHER PUBLICATIONS

Figure 1A:
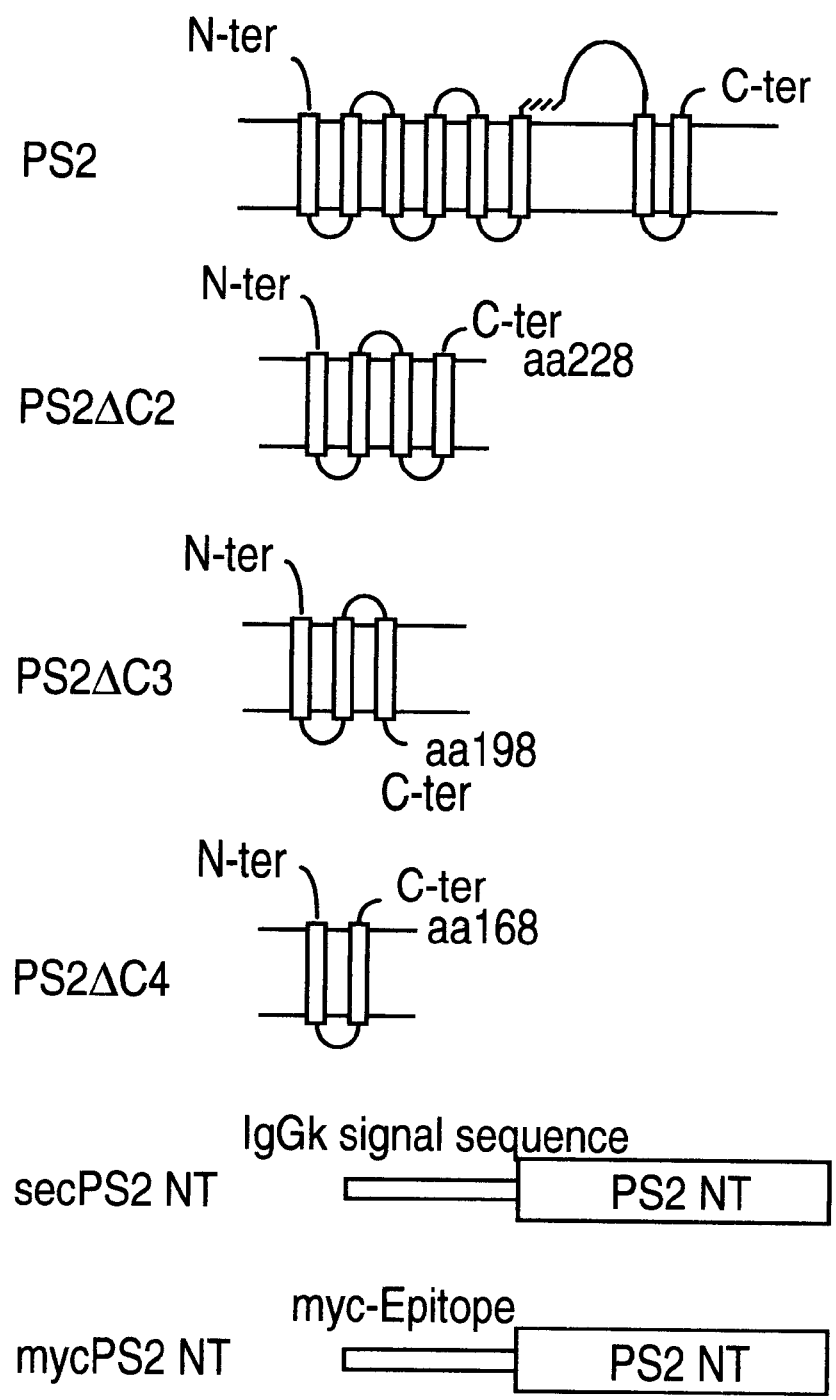

Essalmani et al., Baculovirus–infected cells do not produce the amyloid peptide of Alzheimer's disease from its precursor, FEBS 389, 157–161 (1996).

Ida et al., Analysis of Heterogeneous BA4 Peptides in Human Cerebrospinal Fluid and Blood by a Newly Developed Sensitive Western Blot Assay, The Journal of Biological Chemistry 271 (37), 22908–22914 (1996).

Scheuner et al., Secreted amyloid B–protein similar to that in the senile plaques of Alzheimer's disease is increased in vivo by the presenilin 1 and 2 and APP mutations linked to familial Alzheimer's disease, Nature Medicine 2(8), 864–870 (1996).

Duff et al., Increased amyloid–B42(43) in brains of mice expressing mutant presenilin 1, Nature 383, 710–713 (1996).

Roemer et al., Concepts and strategies for human gene therapy, Eur. J. Biochem 208, 211–225 (1992).

Danos et al., Safe and efficient generation of recombinant retroviruses with amphotropic and ecotropic host ranges, Proc. Natl. Acad. Sci. 85, 6460–6464 (1988).

Borchelt et al., Familial Alzheimer's Disease–Linked Presenilin 1 Variants Elevate AB1–2/1–40 Ratio In Vitro and In Vivo, Neuron 17, 1005–1013 (1996).

Doan et al., Protein Topology of Presenilin 1, Neuron 17, 1023–1030 (1996).

Thinakaran et al., Endoproteolysis of Presenilin 1 and Accumulation of Processed Derivatives In Vivo, Neuron 17, 181–190 (1996).

Akli et al., Transfer of a foreign gene into the brain using adenovirus vectors, Nature Genetics 3, 224–228 (1993).

Podlisny et al., Presenilin Proteins Undergo Heterogeneous Endoproteolysis between Thr291 and Ala299 and Occur as Stable N– and C–Terminal Fragments in Normal and Alzheimer Brain Tissue, Neurobiology 3, 325–337 (1997).

Pradier et al., Biochemical Characterization of Presenilins (S182 & STM2) Proteins, Neurobiological Aging 17, S137 (1996).

Stephens et al., Metabolites of the Beta–Amyloid Precursor Protein Generated by Beta–Secretase Localise to the Trans-Golgi Network and Late Endosome in 293 Cells, Journal of Neuroscience Research 46, 211–225 (1996).

Barelli et al., Characterization of New Polyclonal Antibodies Specific for 40 and 42 AMino Acid–Long Amyloid Beta Peptides: Their Use to Examine the Cell Biology of Presenilins and the Immunohistochemistry of Sporadic Alzheimer's Disease and Cerebral Amyloid Angiopathy Cases, Molecular Medicine 3(10), 695–707 (1997).

Chiocca et al., Transfer and Expression of the lacZ Gene in Rat Brain Neurons Mediated by Herpes Simplex Virus Mutants, The New Biologist 2(8), 739–746 (1990).

Miyanohara et al., Direct Gene Transfer to the Liver with Herpes Simplex Virus Type 1 Vectors: Transient Production of Physiologically Relevant Levels of Circulating Factor IX, The New Biologist 4(3), 238–246 (1992).

Stratford–Perricaude et al., Evaluation of the Transfer and Expression of Mice of an Enzyme–Encoding Gene Using a Human Adenovirus Vector, Human Gene Therapy, 1, 241–256 (1990).

Dobson et al., A Latent, Nonpathogenic HSV–1–Derived Vector Stably Expresses Beta–Galactosidase in Mouse Neurons, Neuron 5, 353–360 (1990).

Xia et al., Enhanced Production and Oligomerization of the 42–residue Amyloid Beta–Protein by Chinese Hamster Ovary Cells Stably Expressing Mutant Presenilins, Journal of Biological Chemistry 272(12), 7977–7982 (1997).

Hartmann et al., Distinct sites of intracellular production for Alzheimer's disease AB40/42 amyloid peptides, Nature Medicine 3(9), 1016–1020 (1997).

Citron et al., Mutant presenilins of Alzheimer's disease increase production of 42–residue amyloid Beta–protein in both transfected cells and transgenic mice, Nature Medicine 3(1), 67–72 (1997).

Weidemann et al, Modulation of APP metabolism by Presenilin–2 Derivatives, Society for Neuroscience Abstracts 23(1–2):1118 (1997).

Haas et al, A technical KO of Amyloid–Beta Pepide, Nature 391:339–340 (1998).

* cited by examiner

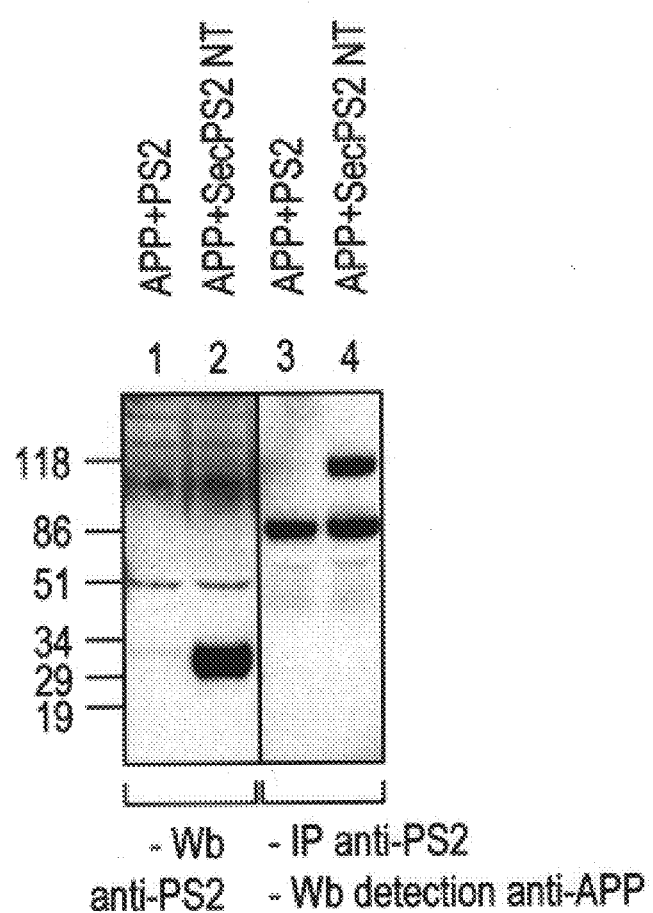

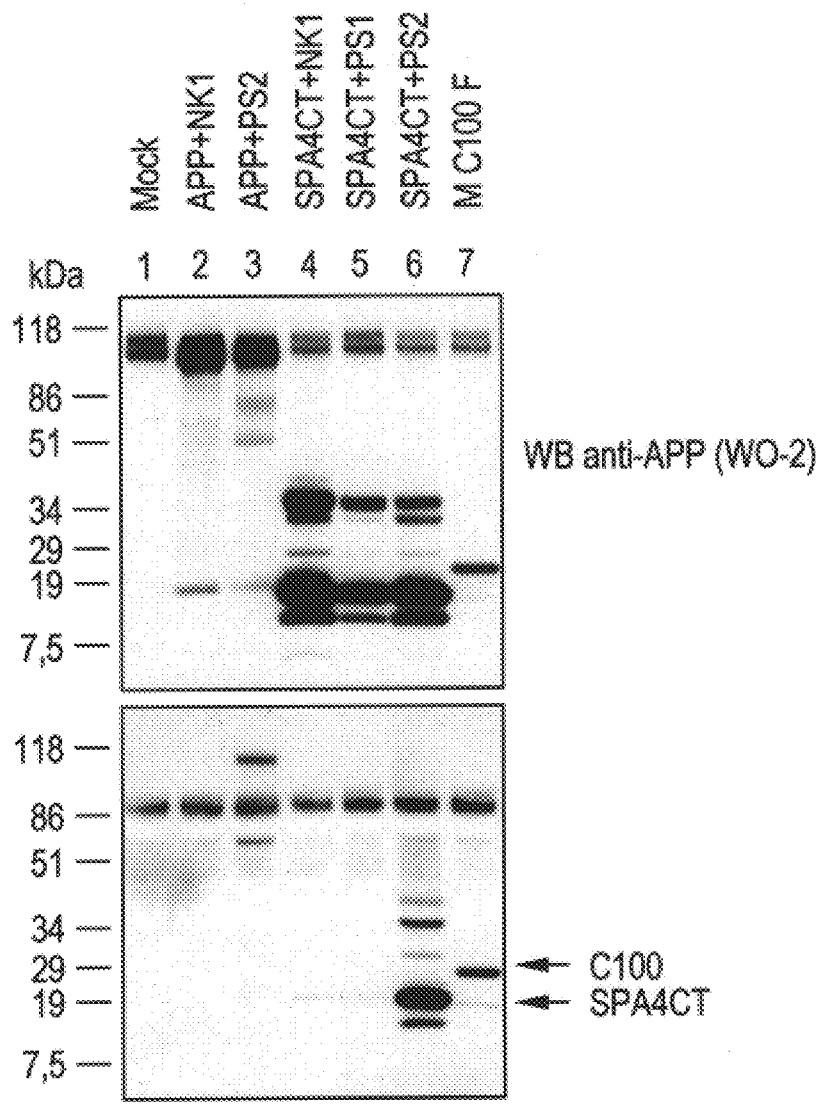

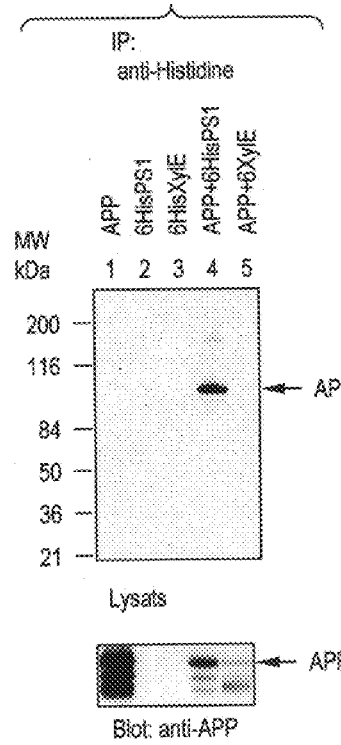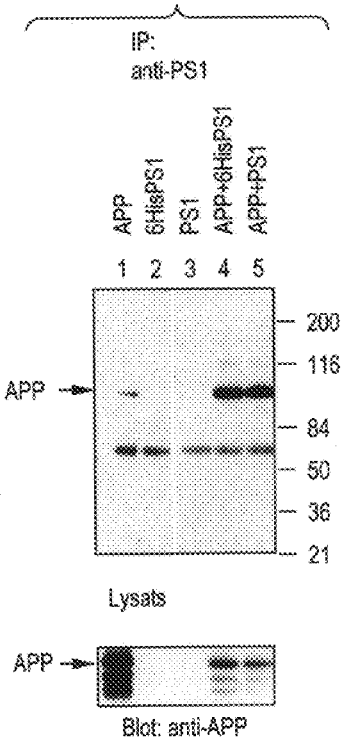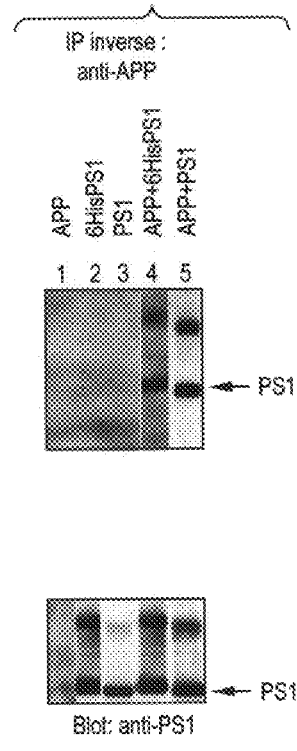

Dose-dependance as a Function of the Concentration of PS2NT

Dose-dependance as a Function of the Concentration of Aβ

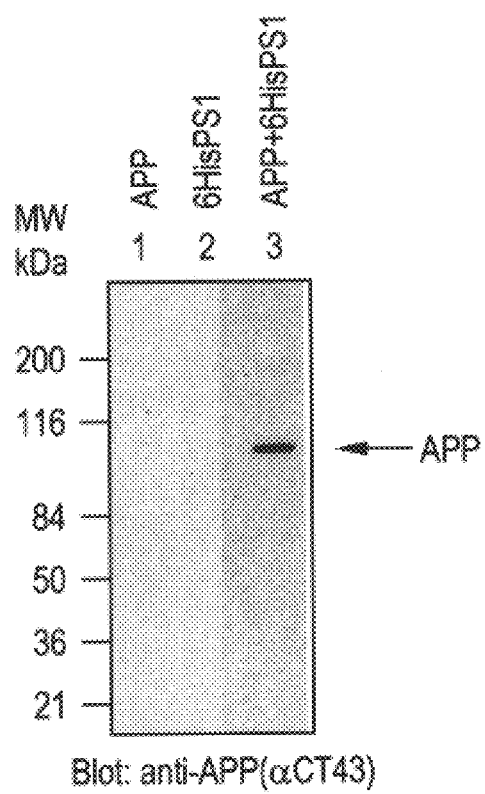
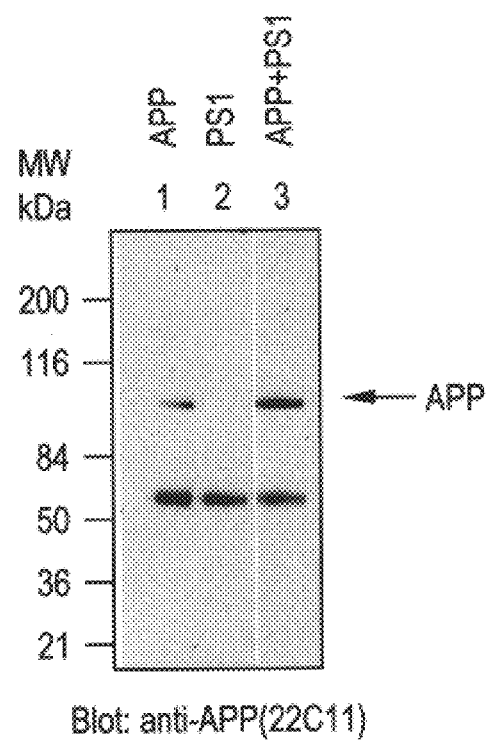

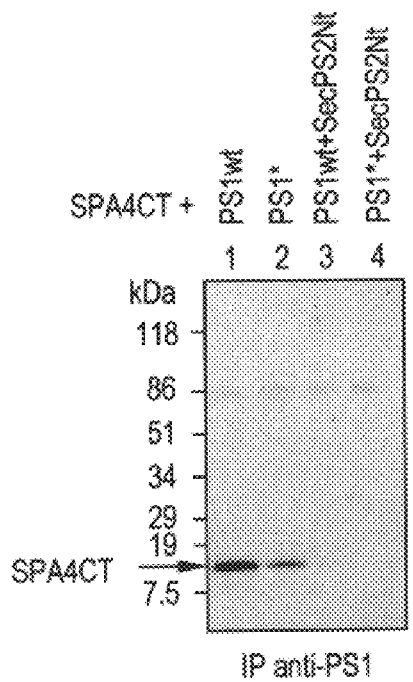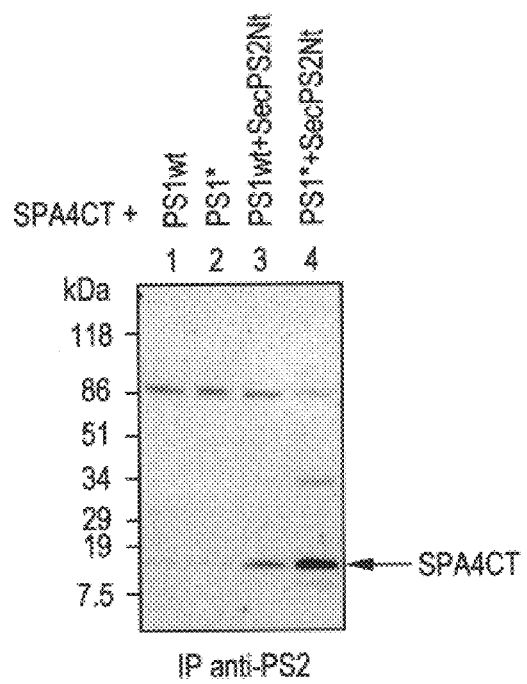

Specificity of the Signal:
Reactivity of PS2NT-K (6nM) with the
βAmyloid Peptides 1-40 and 1-42 in 3mM CHAPS

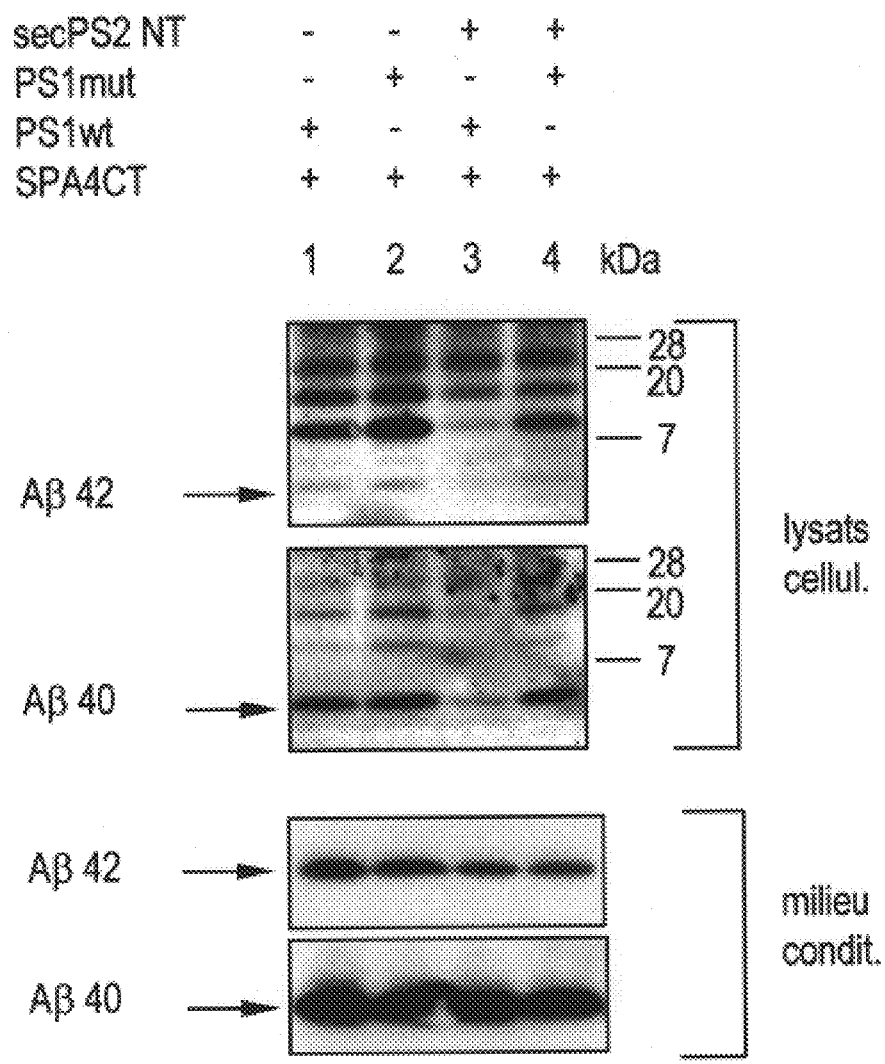

SEQUENCE LISTING

```
<160> NUMBER OF SEQ ID NOS: 15

<210> SEQ ID NO 1
<211> LENGTH: 261
<212> TYPE: DNA
<213> ORGANISM: Homo sapiens
<220> FEATURE:
<221> NAME/KEY: CDS
<222> LOCATION: (1)..(261)

<400> SEQUENCE: 1 atg ctc aca ttc atg gcc tct gac agc gag gaa gaa gtg tgt gat gag      48
Met Leu Thr Phe Met Ala Ser Asp Ser Glu Glu Glu Val Cys Asp Glu
  1               5                  10                  15 cgg acg tcc cta atg tcg gcc gag agc ccc acg ccg cgc tcc tgc cag      96
Arg Thr Ser Leu Met Ser Ala Glu Ser Pro Thr Pro Arg Ser Cys Gln
             20                  25                  30 gag ggc agg cag ggc cca gag gat gga gag aat act gcc cag tgg aga     144
Glu Gly Arg Gln Gly Pro Glu Asp Gly Glu Asn Thr Ala Gln Trp Arg
         35                  40                  45 agc cag gag aac gag gag gac ggt gag gag gac cct gac cgc tat gtc     192
Ser Gln Glu Asn Glu Glu Asp Gly Glu Glu Asp Pro Asp Arg Tyr Val
     50                  55                  60 tgt agt ggg gtt ccc ggg cgg ccg cca ggc ctg gag gaa gag ctg acc     240
Cys Ser Gly Val Pro Gly Arg Pro Pro Gly Leu Glu Glu Glu Leu Thr
 65                  70                  75                  80 ctc aaa tac gga gcg aag cat                                         261
Leu Lys Tyr Gly Ala Lys His
                 85

<210> SEQ ID NO 2
<211> LENGTH: 87
<212> TYPE: PRT
<213> ORGANISM: Homo sapiens

<400> SEQUENCE: 2

Met Leu Thr Phe Met Ala Ser Asp Ser Glu Glu Glu Val Cys Asp Glu
  1               5                  10                  15

Arg Thr Ser Leu Met Ser Ala Glu Ser Pro Thr Pro Arg Ser Cys Gln
             20                  25                  30

Glu Gly Arg Gln Gly Pro Glu Asp Gly Glu Asn Thr Ala Gln Trp Arg
         35                  40                  45

Ser Gln Glu Asn Glu Glu Asp Gly Glu Glu Asp Pro Asp Arg Tyr Val
     50                  55                  60

Cys Ser Gly Val Pro Gly Arg Pro Pro Gly Leu Glu Glu Glu Leu Thr
```

<210> SEQ ID NO 3
<211> LENGTH: 243
<212> TYPE: DNA
<213> ORGANISM: Homo sapiens
<220> FEATURE:
<221> NAME/KEY: CDS
<222> LOCATION: (1)..(243)

<400> SEQUENCE: 3

| | | | | | | | | | | | | | | | | |
|---|---|---|---|---|---|---|---|---|---|---|---|---|---|---|---|---|
| atg | aca | gag | tta | cct | gca | ccg | ttg | tcc | tac | ttc | cag | aat | gca | cag | atg | 48 |
| Met | Thr | Glu | Leu | Pro | Ala | Pro | Leu | Ser | Tyr | Phe | Gln | Asn | Ala | Gln | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tct | gag | gac | aac | cac | ctg | agc | aat | act | gta | cgt | agc | cag | aat | gac | aat | 96 |
| Ser | Glu | Asp | Asn | His | Leu | Ser | Asn | Thr | Val | Arg | Ser | Gln | Asn | Asp | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| aga | gaa | cgg | cag | gag | cac | aac | gac | aga | cgg | agc | ctt | ggc | cac | cct | gag | 144 |
| Arg | Glu | Arg | Gln | Glu | His | Asn | Asp | Arg | Arg | Ser | Leu | Gly | His | Pro | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | tta | tct | aat | gga | cga | ccc | cag | ggt | aac | tcc | cgg | cag | gtg | gtg | gag | 192 |
| Pro | Leu | Ser | Asn | Gly | Arg | Pro | Gln | Gly | Asn | Ser | Arg | Gln | Val | Val | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| caa | gat | gag | gaa | gaa | gat | gag | gag | ctg | aca | ttg | aaa | tat | ggc | gcc | aag | 240 |
| Gln | Asp | Glu | Glu | Glu | Asp | Glu | Glu | Leu | Thr | Leu | Lys | Tyr | Gly | Ala | Lys | |
| 65 | | | | | 70 | | | | | 75 | | | | | 80 | |

| | |
|---|---|
| cat | 243 |
| His | |

<210> SEQ ID NO 4
<211> LENGTH: 81
<212> TYPE: PRT
<213> ORGANISM: Homo sapiens

<400> SEQUENCE: 4

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His

<210> SEQ ID NO 5
<211> LENGTH: 2088
<212> TYPE: DNA
<213> ORGANISM: Homo sapiens
<220> FEATURE:
<221> NAME/KEY: CDS
<222> LOCATION: (1)..(2088)

<400> SEQUENCE: 5

| | | | | | | | | | | | | | | | | |
|---|---|---|---|---|---|---|---|---|---|---|---|---|---|---|---|---|
| atg | ctg | ccc | ggt | ttg | gca | ctg | ctc | ctg | ctg | gcc | gcc | tgg | acg | gct | cgg | 48 |
| Met | Leu | Pro | Gly | Leu | Ala | Leu | Leu | Leu | Leu | Ala | Ala | Trp | Thr | Ala | Arg | |
| 1 | | | | 5 | | | | | 10 | | | | | 15 | | |

```
gcg ctg gag gta ccc act gat ggt aat gct ggc ctg ctg gct gaa ccc       96
Ala Leu Glu Val Pro Thr Asp Gly Asn Ala Gly Leu Leu Ala Glu Pro
         20                  25                  30 cag att gcc atg ttc tgt ggc aga ctg aac atg cac atg aat gtc cag      144
Gln Ile Ala Met Phe Cys Gly Arg Leu Asn Met His Met Asn Val Gln
             35                  40                  45 aat ggg aag tgg gat tca gat cca tca ggg acc aaa acc tgc att gat      192
Asn Gly Lys Trp Asp Ser Asp Pro Ser Gly Thr Lys Thr Cys Ile Asp
 50                  55                  60 acc aag gaa ggc atc ctg cag tat tgc caa gaa gtc tac cct gaa ctg      240
Thr Lys Glu Gly Ile Leu Gln Tyr Cys Gln Glu Val Tyr Pro Glu Leu
 65                  70                  75                  80 cag atc acc aat gtg gta gaa gcc aac caa cca gtg acc atc cag aac      288
Gln Ile Thr Asn Val Val Glu Ala Asn Gln Pro Val Thr Ile Gln Asn
                 85                  90                  95 tgg tgc aag cgg ggc cgc aag cag tgc aag acc cat ccc cac ttt gtg      336
Trp Cys Lys Arg Gly Arg Lys Gln Cys Lys Thr His Pro His Phe Val
            100                 105                 110 att ccc tac cgc tgc tta gtt ggt gag ttt gta agt gat gcc ctt ctc      384
Ile Pro Tyr Arg Cys Leu Val Gly Glu Phe Val Ser Asp Ala Leu Leu
            115                 120                 125 gtt cct gac aag tgc aaa ttc tta cac cag gag agg atg gat gtt tgc      432
Val Pro Asp Lys Cys Lys Phe Leu His Gln Glu Arg Met Asp Val Cys
130                 135                 140 gaa act cat ctt cac tgg cac acc gtc gcc aaa gag aca tgc agt gag      480
Glu Thr His Leu His Trp His Thr Val Ala Lys Glu Thr Cys Ser Glu
145                 150                 155                 160 aag agt acc aac ttg cat gac tac ggc atg ttg ctg ccc tgc gga att      528
Lys Ser Thr Asn Leu His Asp Tyr Gly Met Leu Leu Pro Cys Gly Ile
                165                 170                 175 gac aag ttc cga ggg gta gag ttt gtg tgt tgc cca ctg gct gaa gaa      576
Asp Lys Phe Arg Gly Val Glu Phe Val Cys Cys Pro Leu Ala Glu Glu
            180                 185                 190 agt gac aat gtg gat tct gct gat gcg gag gag gat gac tcg gat gtc      624
Ser Asp Asn Val Asp Ser Ala Asp Ala Glu Glu Asp Asp Ser Asp Val
            195                 200                 205 tgg tgg ggc gga gca gac aca gac tat gca gat ggg agt gaa gac aaa      672
Trp Trp Gly Gly Ala Asp Thr Asp Tyr Ala Asp Gly Ser Glu Asp Lys
210                 215                 220 gta gta gaa gta gca gag gag gaa gaa gtg gct gag gtg gaa gaa gaa      720
Val Val Glu Val Ala Glu Glu Glu Glu Val Ala Glu Val Glu Glu Glu
225                 230                 235                 240 gaa gcc gat gat gac gag gac gat gag gat ggt gat gag gta gag gaa      768
Glu Ala Asp Asp Asp Glu Asp Asp Glu Asp Gly Asp Glu Val Glu Glu
                245                 250                 255 gag gct gag gaa ccc tac gaa gaa gcc aca gag aga acc acc agc att      816
Glu Ala Glu Glu Pro Tyr Glu Glu Ala Thr Glu Arg Thr Thr Ser Ile
            260                 265                 270 gcc acc acc acc acc acc aca gag tct gtg gaa gag gtg gtt cga          864
Ala Thr Thr Thr Thr Thr Thr Glu Ser Val Glu Glu Val Val Arg
            275                 280                 285 gtt cct aca aca gca gcc agt acc cct gat gcc gtt gac aag tat ctc      912
Val Pro Thr Thr Ala Ala Ser Thr Pro Asp Ala Val Asp Lys Tyr Leu
290                 295                 300 gag aca cct ggg gat gag aat gaa cat gcc cat ttc cag aaa gcc aaa      960
Glu Thr Pro Gly Asp Glu Asn Glu His Ala His Phe Gln Lys Ala Lys
305                 310                 315                 320 gag agg ctt gag gcc aag cac cga gag aga atg tcc cag gtc atg aga     1008
Glu Arg Leu Glu Ala Lys His Arg Glu Arg Met Ser Gln Val Met Arg
                325                 330                 335
```

-continued

| | |
|---|---|
| gaa tgg gaa gag gca gaa cgt caa gca aag aac ttg cct aaa gct gat<br>Glu Trp Glu Glu Ala Glu Arg Gln Ala Lys Asn Leu Pro Lys Ala Asp<br>            340                    345                      350 | 1056 |
| aag aag gca gtt atc cag cat ttc cag gag aaa gtg gaa tct ttg gaa<br>Lys Lys Ala Val Ile Gln His Phe Gln Glu Lys Val Glu Ser Leu Glu<br>        355                    360                    365 | 1104 |
| cag gaa gca gcc aac gag aga cag cag ctg gtg gag aca cac atg gcc<br>Gln Glu Ala Ala Asn Glu Arg Gln Gln Leu Val Glu Thr His Met Ala<br>370                    375                    380 | 1152 |
| aga gtg gaa gcc atg ctc aat gac cgc cgc ctg gcc ctg gag aac<br>Arg Val Glu Ala Met Leu Asn Asp Arg Arg Leu Ala Leu Glu Asn<br>385                  390                  395                400 | 1200 |
| tac atc acc gct ctg cag gct gtt cct cct cgg cct cgt cac gtg ttc<br>Tyr Ile Thr Ala Leu Gln Ala Val Pro Pro Arg Pro Arg His Val Phe<br>            405                    410                    415 | 1248 |
| aat atg cta aag aag tat gtc cgc gca gaa cag aag gac aga cag cac<br>Asn Met Leu Lys Lys Tyr Val Arg Ala Glu Gln Lys Asp Arg Gln His<br>                420                    425                    430 | 1296 |
| acc cta aag cat ttc gag cat gtg cgc atg gtg gat ccc aag aaa gcc<br>Thr Leu Lys His Phe Glu His Val Arg Met Val Asp Pro Lys Lys Ala<br>            435                    440                    445 | 1344 |
| gct cag atc cgg tcc cag gtt atg aca cac ctc cgt gtg att tat gag<br>Ala Gln Ile Arg Ser Gln Val Met Thr His Leu Arg Val Ile Tyr Glu<br>450                    455                    460 | 1392 |
| cgc atg aat cag tct ctc tcc ctg ctc tac aac gtg cct gca gtg gcc<br>Arg Met Asn Gln Ser Leu Ser Leu Leu Tyr Asn Val Pro Ala Val Ala<br>465                  470                  475                480 | 1440 |
| gag gag att cag gat gaa gtt gat gag ctg ctt cag aaa gag caa aac<br>Glu Glu Ile Gln Asp Glu Val Asp Glu Leu Leu Gln Lys Glu Gln Asn<br>                    485                    490                    495 | 1488 |
| tat tca gat gac gtc ttg gcc aac atg att agt gaa cca agg atc agt<br>Tyr Ser Asp Asp Val Leu Ala Asn Met Ile Ser Glu Pro Arg Ile Ser<br>                500                    505                    510 | 1536 |
| tac gga aac gat gct ctc atg cca tct ttg acc gaa acg aaa acc acc<br>Tyr Gly Asn Asp Ala Leu Met Pro Ser Leu Thr Glu Thr Lys Thr Thr<br>            515                    520                    525 | 1584 |
| gtg gag ctc ctt ccc gtg aat gga gag ttc agc ctg gac gat ctc cag<br>Val Glu Leu Leu Pro Val Asn Gly Glu Phe Ser Leu Asp Asp Leu Gln<br>530                    535                    540 | 1632 |
| ccg tgg cat tct ttt ggg gct gac tct gtg cca gcc aac aca gaa aac<br>Pro Trp His Ser Phe Gly Ala Asp Ser Val Pro Ala Asn Thr Glu Asn<br>545                  550                  555                560 | 1680 |
| gaa gtt gag cct gtt gat gcc cgc cct gct gcc gac cga gga ctg acc<br>Glu Val Glu Pro Val Asp Ala Arg Pro Ala Ala Asp Arg Gly Leu Thr<br>                    565                    570                    575 | 1728 |
| act cga cca ggt tct ggg ttg aca aat atc aag acg gag gag atc tct<br>Thr Arg Pro Gly Ser Gly Leu Thr Asn Ile Lys Thr Glu Glu Ile Ser<br>            580                    585                    590 | 1776 |
| gaa gtg aag atg gat gca gaa ttc cga cat gac tca gga tat gaa gtt<br>Glu Val Lys Met Asp Ala Glu Phe Arg His Asp Ser Gly Tyr Glu Val<br>595                    600                    605 | 1824 |
| cat cat caa aaa ttg gtg ttc ttt gca gaa gat gtg ggt tca aac aaa<br>His His Gln Lys Leu Val Phe Phe Ala Glu Asp Val Gly Ser Asn Lys<br>610                    615                    620 | 1872 |
| ggt gca atc att gga ctc atg gtg ggc ggt gtt gtc ata gcg aca gtg<br>Gly Ala Ile Ile Gly Leu Met Val Gly Gly Val Val Ile Ala Thr Val<br>625                  630                  635                640 | 1920 |
| atc gtc atc acc ttg gtg atg ctg aag aag aaa cag tac aca tcc att<br>Ile Val Ile Thr Leu Val Met Leu Lys Lys Lys Gln Tyr Thr Ser Ile | 1968 |

```
                            645                 650                 655
cat cat ggt gtg gtg gag gtt gac gcc gct gtc acc cca gag gag cgc      2016
His His Gly Val Val Glu Val Asp Ala Ala Val Thr Pro Glu Glu Arg
                660                 665                 670 cac ctg tcc aag atg cag cag aac ggc tac gaa aat cca acc tac aag      2064
His Leu Ser Lys Met Gln Gln Asn Gly Tyr Glu Asn Pro Thr Tyr Lys
            675                 680                 685 ttc ttt gag cag atg cag aac tag                                      2088
Phe Phe Glu Gln Met Gln Asn
        690                 695

<210> SEQ ID NO 6
<211> LENGTH: 695
<212> TYPE: PRT
<213> ORGANISM: Homo sapiens

<400> SEQUENCE: 6

Met Leu Pro Gly Leu Ala Leu Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300
```

-continued

```
Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
        340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 7
<211> LENGTH: 38
<212> TYPE: DNA
```

```
<213> ORGANISM: Artificial Sequence
<220> FEATURE:
<223> OTHER INFORMATION: Description of Artificial Sequence:PCR Primer
      Oligonucleotide

<400> SEQUENCE: 7
cggaattcat cgattccacc atgctcacat tcatggcc                              38

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence:PCR Primer
      Oligonucleotide

<400> SEQUENCE: 8
ccgctcgagt cattgtcgac catgcttcgc tccgtatttg agg                        43

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:PCR Primer
      Oligonucleotide

<400> SEQUENCE: 9
caaagatctg atgcagaatt ccgacat                                          27

<210> SEQ ID NO 10
<211> LENGTH: 59
<212> TYPE: DNA
<213> ORGANISM: Artificial Sequence
<220> FEATURE:
<223> OTHER INFORMATION: Description of Artificial Sequence:PCR Primer
      Oligonucleotide

<400> SEQUENCE: 10
caagcggccg ctcatccctt gtcatcgtcg tccttgtagt ctccgttctg catctgctc       59

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:PCR Primer
      Oligonucleotide

<400> SEQUENCE: 11
caaagatcta agaaacagta cacatcc                                          27

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:PCR Primer
      Oligonucleotide

<400> SEQUENCE: 12
ccatcgatgg ctacatcttc acttcagag                                        29

<210> SEQ ID NO 13
<211> LENGTH: 31
<212> TYPE: DNA
<213> ORGANISM: Artificial Sequence
```

```
-continued

<220> FEATURE:
<223> OTHER INFORMATION: Description of Artificial Sequence:PCR Primer
      Oligonucleotide

<400> SEQUENCE: 13
ccatcgatgg ctatttttga tgatgaactt c                                    31

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:PCR Primer
      Oligonucleotide

<400> SEQUENCE: 14
ccgtggagct cctcccg                                                    17

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence:H1 Synthetic
      Peptide

<400> SEQUENCE: 15

Lys Thr Pro Lys Lys Ala Lys Lys Pro Lys Thr Pro Lys Lys Ala Lys
 1               5                  10                  15

Lys Pro
```

INTERACTION TEST FOR THE INVESTIGATION OF INHIBITORY MOLECULES OF THE INTERACTION BETWEEN A PRESENILIN AND THE β-AMYLOID PEPTIDE

This application is a Continuation Application of PCT application PCT/FR98/02278, which designated the United States of America and which was filed Oct. 23, 1998. This application also claims the benefit of U.S. provisional application No. 60/103,553, which was filed Oct. 8, 1998, the disclosure of which is incorporated herein by reference in its entirety.

The present invention relates to novel peptide and nucleotide sequences. More particularly, the present invention relates to novel polypeptides capable of inhibiting at least in part the interaction between presenilin 1 or presenilin 2 on the one hand and the precursor of the β-amyloid peptide and/or the β-amyloid peptide on the other hand. The present invention also relates to the development of in vitro tests for the demonstration of molecules and in particular of small molecules capable of inhibiting this interaction.

The Aβ amyloid peptide, of 37 to 42 amino acids, is the principal protein component of characteristic senile plaques of Alzheimer's disease. This peptide is produced by cleavage of its precursor, the precursor protein of amyloid peptide (APP). Mutations in the gene of the APP are responsible for certain early familial forms of Alzheimer's disease. However, the majority of these forms are connected with the presence of mutations on two genes, presenilins PS1 (initially called S182) and PS2 (initially STM2), recently identified by positional cloning (Hardy, 1997). These forms are dominant and these anomalies all correspond to missense mutations with the exception of one involving the deletion of an exon. The presenilins are hydrophobic membrane proteins of molecular mass of approximately 45–50 kDa and which have 67% identity between them. They are homologous with two proteins of *C. elegans*, SPE4 and Sel-12, which are respectively involved indirectly in intracellular transport and in the signalling of the Notch receptors. However, the physiological function of the presenilins is still unknown. Involvement in Alzheimer's disease of two so closely related proteins suggests that the presenilins contribute to an essential physiological route in the aetiology of this pathology.

The protein PS1 comprises 467 amino acids and PS2 comprises 448. Both of them have the structure of a membrane protein with 6 to 8 potential transmembrane domains. Each of the presenilins is subject in vivo to precise proteolytic cleavage resulting in two fragments generally called N(amino)- and C(carboxy)-terminal fragments (Thinakaran et al., 1996). This cleavage has been mapped between the residues 291 and 299 of PS1 (Podlisny et al., 1997) and in a homologous region of PS2. N-terminal (N-ter) fragment is thus in general understood as meaning the fragment from position 1 to approximately 291 of PS1 and C-terminal fragment is understood as meaning the remainder. Although the exact topology of the presenilins in the lipid membranes has not been clearly established, it is proposed that their N- and C-terminal[RC1] ends, as well as the large hydrophilic loop, are present in the cytosol compartment (Doan et al., 1996, see Scheme FIG. 1).

It has now been demonstrated that the mutated forms of the presenilins induce the increase in the production of the long amyloid peptide Aβ 1–42 with respect to that of Aβ 1–40 as much in carrier patients (Scheuner et al., 1996), as in transfected cells (Borchelt et al., 1996) or in transgenic mice (Duff et al., 1996). The amyloid peptide Aβ, which forms senile plaques, lesions characteristic of the pathology, and its different forms are derived from the catabolism of the amyloid precursor protein, APP. In particular, two essential forms of the amyloid peptide have been described, one of forty residues, Aβ40, and the other having two additional residues in its carboxy terminal, Aβ42. In vitro, the peptide Aβ has strong aggregation properties which are increased for the form Aβ42 and the latter effectively seems to form the first aggregates detectable in the pathology. In addition, the form Aβ42 is specifically produced after cranial trauma in man, which constitutes one of the best established environmental risk factors of Alzheimer's disease. Moreover, the early genetic forms of the disease connected with mutations as much on APP (there are six of them) as now on the presenilins 1 and 2, all contribute to an increase in the Aβ42/Aβ40 ratio. All of these factors seem to point to Aβ42 as the key agent of the pathology as much in the genetic forms as in the sporadic forms of the disease and the elucidation of its mechanism of formation has become a fundamental question.

In this respect, complex formation in the same cell envelope between the precursor of the β-amyloid peptide and PS1 or PS2 has been reported (Weidemann et al., 1997, Xia et al., 1997), however, the precise nature of the events responsible for the production of the β-amyloid peptide is not known and no link has yet been able to be established between the possible role of these complexes and the production of the β-amyloid peptide Aβ42. It is nevertheless important to note that the peptide Aβ42, but not Aβ40, seem to be localized in the endoplasmic reticulum in neuronal cells (Hartmann et al., 1997).

The present invention results from the identification and the characterization by the Applicant of particular regions of presenilin 1 (PS1) and of presenilin 2 (PS2), as well as of particular regions of the β-amyloid precursor peptide (APP) involved in the formation of APP/PS1 and APP/PS2 complexes.

The present invention follows in particular from the demonstration of the capacity of the N-terminal hydrophilic region (amino acids 1–87) of PS2 to recognize different domains of APP. It additionally follows from the demonstration of similar properties for the N-terminal region of PS1 (fragment 1-213). It likewise results from the demonstration of the capacity of the polypeptides derived from the presenilin regions defined above to inhibit the formation of complexes between APP and the presenilins. The presenilins of the present application correspond essentially to presenilin 1 (PS1) and/or to presenilin 2 (PS2).

The present invention additionally results from the demonstration of the unexpected special cellular location of the regions in interaction with respect to the lipid membrane. It results more particularly from the fact that these interactions can take place not only at the membrane level but also at the level of the lumen of the endoplasmic reticulum and in the extracellular compartment. This is unexpected inasmuch as the N-terminal region of the PS (involved in the interaction) is generally considered as being localized in the cytoplasm under standard conditions.

The characterization of the domains of interaction of APP and of the presenilins and the demonstration of the different cellular locations of these interactions allow the preparation of novel polypeptides which can be utilized pharmaceutically to be envisaged.

A first subject of the invention thus relates to polypeptides capable of inhibiting at least in part the interaction between a presenilin and the precursor of the β-amyloid peptide and/or the β-amyloid peptide.

In the sense of capable of inhibiting the interaction, it is understood that the presence of the polypeptides of the invention and/or of the ligands and/or molecules demonstrated with the aid of the process of the invention suffice to inhibit at least partially the said interaction between a presenilin and/or its N-terminal end and the precursor of the β-amyloid peptide and/or the β-amyloid peptide and preferably the Aβ$_{1-42}$ peptide.

It is demonstrated in the examples of the present application that the inhibition of this interaction with one of the polypeptides of the invention leads to a decrease in the production of the Aβ$_{1-42}$ intracellular amyloid peptide. This functional consequence is thus envisaged for any polypeptide of the invention and/or ligands and/or molecules demonstrated with the aid of the process of the invention. To inhibit this interaction and thus to inhibit the production of Aβ$_{1-42}$ as a consquence represents a therapeutic target of choice in the diseases involving this form of the amyloid peptide.

According to a particular embodiment, the polypeptides according to the invention have at least one part of presenilin 2 (PS2) allowing the interaction with the precursor of the β-amyloid peptide and/or the β-amyloid peptide. Preferably, the polypeptides according to the invention are characterized in that the part of PS2 corresponds to the N-terminal hydrophilic fragment of PS2. More preferentially, the polypeptides according to the invention comprise all or part of the sequence corresponding to the sequence SEQ ID NO:2 or of a sequence derived from this.

According to another embodiment, the polypeptides according to the invention have at least one part of PS1 allowing interaction with the precursor of the β-amyloid peptide and/or the β-amyloid peptide. Preferably, the polypeptides according to the invention comprise all or part of the sequence corresponding to the sequence SEQ ID NO:4 or of a sequence derived from this.

According to another embodiment, the polypeptides according to the invention comprise at least the common regions of homology corresponding to the sequences SEQ ID NO:2 and SEQ ID NO:4 respectively According to another embodiment, the polypeptides according to the invention have at least one part of the precursor of the β-amyloid peptide (APP). Preferably, the polypeptides according to the invention contain a part of APP outside the region corresponding to the β-amyloid peptide. Even more preferably, the polypeptides are characterized in that the part of the precursor of the β-amyloid peptide comprises all or part of the fragment 1-596. More preferably, the polypeptides according to the invention contain all or part of a sequence chosen from tamongst the sequence corresponding to the fragment 1-596 of the sequence SEQ ID NO:6, or a derived sequence.

In the sense of the present invention, the term derived polypeptide sequence denotes any polypeptide sequence differing from polypeptide sequences corresponding to the sequences presented in SEQ ID NO:2 or SEQ ID NO:4 respectively, or the denoted fragments of SEQ ID NO:6, obtained by one or more modifications of genetic and/or chemical nature, and having the capacity to inhibit at least in part the interaction between presenilin 1 or presenilin 2 and the precursor of the β-amyloid peptide and/or the β-amyloid peptide. Modification of genetic and/or chemical nature should be understood as meaning any mutation, substitution, deletion, addition and/or modification of one or more residues. Such derivatives can be generated with different aims, such as, especially, that of increasing the affinity of the peptide for its site of interaction, that of improving its level of production, that of increasing its resistance to proteases, that of increasing its therapeutic efficacy or of reducing its secondary effects, or that of conferring on it novel pharmacokinetic and/or biological properties.

The invention likewise provides non-peptide or not exclusively peptide compounds which can be used pharmaceutically. In fact, it is possible, starting from the polypeptide motifs described in the present application, to produce molecules which inhibit at least partially the interaction between presenilin 1 or presenilin 2 and the precursor of the β-amyloid peptide and/or the β-amyloid peptide, and which are not exclusively peptide and are compatible with pharmaceutical use. In this respect, the invention relates to the use of polypeptides such as described above for the preparation of non-peptide, or not exclusively peptide, pharmacologically active molecules by determination of the structural elements of these polypeptides which are important for their activity and reproduction of these elements by non-peptide or not exclusively peptide structures. The invention also relates to pharmaceutical compositions comprising one or more molecules prepared in this way.

The polypeptides according to the invention should comprise sequences allowing precise cellular localization in order to inhibit the interaction between the presenilins and the precursor of the β-amyloid peptide and/or the β-amyloid peptide. Preferentially, these are the polypeptides derived from SEQ ID NO:2 and SEQ ID NO:4 respectively which comprise exogenous cell localization sequences and more preferably still, a polypeptide comprising the N-terminal end of PS1 or PS2. Amongst these sequences, it is possible to mention signal peptide sequences such as the signal peptide sequence of IgkB, the signal peptide of APP, the signal peptides of subunits of the nicotinic receptors of muscular and central acetylcholine etc. . . .

Among the polypeptides of particular interest, there may be mentioned a polypeptide comprising the 87 first residues of the N-terminal end of PS2 and the IgkB signal peptide.

The present invention likewise relates to any nucleotide sequence coding for a peptide capable of inhibiting at least in part the interaction between presenilin 1 or presenilin 2 and the precursor of the β-amyloid peptide and/or the β-amyloid peptide.

According to a particular embodiment, it is a nucleotide sequence comprising all or part of the nucleotide sequence SEQ ID NO:1 or of a sequence derived from this. According to another embodiment, it is a nucleotide sequence comprising all or part of the nucleotide sequence SEQ ID NO:3 or of a sequence derived from this. Preferably, it is a nucleotide sequence comprising the zones of homologies common to the nucleotide sequences SEQ ID NO:1 and SEQ ID NO:3 respectively According to another embodiment, it is the nucleotide sequence corresponding to the fragment 1-596 (nucleic acids 1 to 1788) of the sequence SEQ ID NO:6(SEQ ID NO:5), or a derived sequence.

In the sense of the present invention, the term derived nucleotide sequence denotes any sequence different from the considered sequence because of the degeneration of the genetic code, obtained by one or more modifications of genetic and/or chemical nature, as well as any sequence hybridizing with these sequences or fragments of these and coding for a polypeptide according to the invention. Modification of genetic and/or chemical nature can be understood as meaning any mutation, substitution, deletion, addition and/or modification of one or more residues. The term derivative likewise comprises the sequences homologous with the considered sequence, originating from other cell sources and especially from cells of human origin, or from other organisms. Such homologous sequences can be obtained by hybridization experiments. The hybridizations can be carried out starting from nucleic acid banks, using, as a probe, the native sequence or a fragment of this, under variable hybridization conditions (Maniatis et al., 1982).

Nucleotide sequences according to the invention can be of artificial or non-artificial origin. They can be genomic sequences, of cDNA, of RNA, of hybrid sequences or of synthetic or semi-synthetic sequences. These sequences can be obtained, for example, by screening DNA banks (cDNA bank, genomic DNA bank) by means of probes elaborated on the basis of sequences shown above. Such banks can be prepared starting from cells of different origins by conventional techniques of molecular biology known to the person skilled in the art. The nucleotide sequences of the invention can likewise be prepared by chemical synthesis or even by mixed methods including the chemical or enzymatic modification of sequences obtained by screening of banks. Generally speaking, the nucleic acids of the invention can be prepared according to any technique known to the person skilled in the art.

Another subject of the present invention relates to a process for the preparation of the polypeptides of the invention according to which a cell containing a nucleotide sequence according to the invention is cultured under conditions of expression of the said sequence and the polypeptide produced is recovered. In this case, the part coding for the said polypeptide is generally placed under the control of signals allowing its expression in a cell host. The choice of these signals (promoters, terminators, secretion leader sequence, etc.) can vary as a function of the cell host used. In addition, the nucleotide sequences of the invention can be part of a vector which can be an autonomous or integrative replication vector. More particularly, autonomous replication vectors can be prepared using autonomous replication sequences in the chosen host. When integrative vectors are involved, these can be prepared, for example, using sequences homologous to certain regions of the genome of the host, allowing, by homologous recombination, the integration of the vector.

The present invention likewise relates to host cells transformed with a nucleic acid having a nucleotide sequence according to the invention. The cell hosts which can be used for the production of the peptides of the invention by the recombinant route are eukaryotic or prokaryotic hosts as well. Amongst the eukaryotic hosts which are suitable, it is possible to mention animal cells, yeasts or fungi. In particular, when yeasts are concerned, it is possible to mention yeasts of the genus Saccharomyces, Kluyveromyces, Pichia, Schwanniomyces or Hansenula. When they are animal cells, it is possible to mention COS, CHO, C127, human neuroblastoma cells etc. Amongst the fungi, it is more particularly possible to mention Aspergillus ssp. or Trichoderma ssp. As prokaryotic hosts, it is preferred to use the following bacteria: *E. coli*, Bacillus or Streptomyces.

According to a preferred embodiment, the host cells are advantageously represented by recombinant yeast strains for the expression of the nucleic acids of the invention as well as the production of the proteins derived from these.

Preferentially, the host cells comprise at least one sequence or a sequence fragment chosen from amongst the sequences SEQ ID NO:1 or SEQ ID NO:3 respectively, or the denoted fragments of SEQ ID NO:5 for the production of polypeptides according to the invention.

The nucleotide sequences according to the invention can be used in the context of gene therapy, in particular through the addition of a signal peptide for the derivatives of SEQ ID NO:1 and SEQ ID NO:3 respectively, for the production and transfer in vivo of polypeptides capable of inhibiting at least in part the interaction between presenilin 1 or presenilin 2 and the precursor of the β-amyloid peptide and/or the β-amyloid peptide. In fact, unexpectedly, it has been demonstrated in the present application that a signal peptide is necessary for the addressing of the polypeptides of the invention in the lumen of the endoplasmic reticulum and thus for conferring on the polypeptides derived from the sequences SEQ ID NO:2 and SEQ ID NO:4 respectively a biological activity with the aim of inhibiting the interaction between the presenilins and the precursor of the β-amyloid peptide and/or the β-amyloid peptide.

According to another embodiment of the invention, the nucleotide sequences of the invention are used for the construction of an expression cassette, which can be used in an expression vector. In particular, the expression cassette serves for the production of the polypeptides according to the invention.

The polypeptides of the invention can be obtained by expression in a cell host of a nucleotide sequence such as described above, incorporated or not incorporated in a recombinant DNA, using techniques known to the person skilled in the art, or by a combination of these techniques.

Preferentially, the nucleic sequences according to the invention are part of a vector which is useful for inducing in vivo, ex vivo and/or in vitro the expression of the claimed polypeptides. The vector used can be of various origins, since it is capable of transforming animal cells, preferably human nerve cells. It can be a viral vector, non-viral vector or a plasmid vector. In a preferred embodiment of the invention, a viral vector is used which can be derived from adenoviruses, retroviruses, adeno-associated viruses (AAVs), from herpesvirus, from cytomegalovirus (CMV), from vaccinia virus, etc. Vectors derived from adenoviruses, from retroviruses or from AAVs incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

The present invention thus likewise relates to any recombinant virus comprising, inserted in its genome, a nucleic sequence such as defined above coding for a polypeptide of the invention.

Advantageously, the recombinant virus according to the invention is a defective virus. The term "defective virus" denotes a virus incapable of replicating in the target cell. Generally, the genome of the defective viruses used within the context of the present invention is thus devoid at least of the sequences necessary for the replication of the said virus in the infected cell. These regions can be either eliminated (all or in part), rendered non-functional, or substituted by other sequences and especially by the nucleic acid of the invention.

Preferentially, the defective virus nevertheless conserves the sequences of its genome which are necessary for the encapsidation of the viral particles.

It is particularly advantageous to use the nucleic sequences of the invention in incorporated form with an adenovirus, an AAV or a defective recombinant retrovirus. According to a preferred embodiment, it is an adenovirus.

Different serotypes of adenovirus exist whose structure and properties vary somewhat. Amongst these serotypes, it is preferred to use within the context of the present invention the human adenoviruses of type 2 or 5 (Ad 2 or Ad 5) or the adenoviruses of animal origin (see Application WO94/26914). Amongst the adenoviruses of animal origin which can be used within the context of the present invention, it is possible to mention the adenoviruses of canine, bovine, murine, (example: Mav1, Beard et al., Virology 75 (1990) 81), ovine, porcine, avian or even simian origin (example: SAV). Preferably, the adenovirus of animal origin is a canine adenovirus, more preferentially a CAV2 adenovirus [manhattan or A26/61 strain (ATCC VR-800) for example]. Preferably, adenoviruses of human or canine or mixed origin are used within the context of the invention. Preferentially, in the genome of the adenoviruses of the invention, the region E1 at least is non-functional. The viral gene considered can be rendered non-functional by any technique known to the person skilled in the art, and especially by total suppression, substitution, partial deletion, or addition of one or more bases in the gene or genes considered. Other regions can likewise be modified, and especially the E3 (WO95/02697), E2 (WO94/28938), E4 (WO94/28152, WO94/12649, WO95/02697) and L5 (WO95/02697) region. According to a preferred embodiment, the adenovirus comprises a deletion in the regions E1 and E4. According to another preferred embodiment, it comprises a deletion in the region E1 at the level of which are inserted the region E4 and the coding sequence. In the viruses of the invention, the deletion in the region E1 preferentially extends from nucleotides 455 to 3329 in the sequence of the adenovirus Ad5. According to another preferred embodiment, the exogenous nucleic acid sequence is inserted at the level of the deletion in the E1 region.

The defective recombinant viruses of the invention can be prepared by homologous recombination between a defective virus and a plasmid carrying, inter alia, the nucleotide sequence such as defined above (Levrero et al., Gene 101 (1991) 195; Graham, EMBO J. 3(12) (1984) 2917). Homologous recombination takes place after cotransfection of the said viruses and plasmid in an appropriate cell line. The cell line used must preferably (i) be transformable by the said elements, and (ii) contain sequences capable of complementing the part of the genome of the defective virus, preferably in integrated form to avoid the risks of recombination. By way of example of a line which can be used for the preparation of defective recombinant adenoviruses, it is possible to mention the human embryonic kidney line 293 (Graham et al., J. Gen. Virol. 36 (1977) 59) which especially contains, integrated in its genome, the left part of the genome of an Ad5 adenovirus (12%). By way of example of a line which can be used for the preparation of defective recombinant retroviruses, it is possible to mention the CRIP line (Danos and Mulligan, PNAS 85 (1988) 6460). Next, the viruses which have multiplied are recovered and purified according to the conventional techniques of molecular biology.

The present application likewise relates to defective recombinant viruses comprising a heterologous nucleic sequence coding for a polypeptide according to the invention.

Another subject of the invention resides in polyclonal or monoclonal antibodies or antibody fragment. Such antibodies can be generated by methods known to the person skilled in the art. In particular, these antibodies can be prepared by immunization of an animal against a polypeptide whose sequence is chosen from amongst the sequences SEQ ID NO:2 or SEQ ID NO:4 respectively, or the denoted fragments of SEQ ID NO:6, then taking of a sample of the blood and isolation of the antibodies. These antibodies can likewise be generated by preparation of hybridomas according to techniques known to the person skilled in the art. The antibodies or antibody fragment according to the invention can especially be used to inhibit at least in part the interaction between presenilin 1 or presenilin 2 and the precursor of the β-amyloid peptide and/or the β-amyloid peptide.

Another object of the present invention relates to a process for identifying compounds capable of modulating or of inhibiting at least in part the interaction between presenilin 1 or presenilin 2 and the precursor of the β-amyloid peptide and/or the β-amyloid peptide. In particular, the process can be used as a test for screening molecules to identify such inhibitor compounds.

This test is based, in particular, on the detection of the inhibition of the interaction between the presenilins (1 or 2) and the APP or the Aβ peptide generally and between the $A\beta_{1-42}$ peptide and the N-terminal end of PS2 particularly. In fact, with the aid of marker proteins attached to the presenilins or fragments of these and appropriate visualization systems and especially by immunoprecipitation, use of chromophores or fluophores, it is quite possible to detect an inhibition in the interaction of the proteins or fragments of these mentioned above. Such a process thus comprises at least one labelling step of the presenilins and/or of the APP or of the fragments of these and a step of detection of the inhibition of the interaction either between the $A\beta_{1-42}$ peptide and the N-terminal end of the presenilins and preferentially PS2, or between the complete APP proteins and presenilins.

According to a first embodiment of the process, the demonstration and/or identification of such compounds is carried out according to the following steps:

The $A\beta_{1-42}$ peptide is absorbed beforehand on a nitrocellulose membrane by incubation.

a bacterial extract containing all or part of a presenilin (PS1 or PS2) and advantageously the N-terminal end, is then added for incubation with the molecule or a mixture containing different molecules to be tested After washing, the interaction of the presenilin with the $A\beta_{1-42}$ peptide on the nitrocellulose filter is demonstrated with the aid of presenilin marker proteins. The molecules sought inhibit the interaction and thus decrease the intensity of the signal of the marker proteins.

The marker proteins used are advantageously a) the immobilizing protein of the S-tag, coupled to alkaline phosphatase or to a fluorescent chromophore, or b) an anti-PSNT antibody, that is to say directed against the N-terminal end of a presenilin.

According to another embodiment of the process, the investigation of novel compounds is carried out in the following manner:

the Aβ42 peptide is incubated beforehand on a plate containing wells (96-well format or greater)

the N-terminal end of a purified recombinant presenilin is then added with the molecule or a mixture containing different molecules to be tested, for incubation After washing, the interaction of presenilin with the $A\beta_{1-42}$ peptide in the plate is demonstrated with the aid of presenilin marker proteins. The loss of interaction between the presenilins and the precursor of the β-amyloid peptide and/or the β-amyloid peptide is detected by spectrophotometry.

In the precise case of the use of the immobilizing protein of the S-tag coupled to alkaline phosphatase as marker protein, after visualization with a colorimetric substrate, the signal is detected at 450 nm.

According to an advantageous and preferred embodiment of the process, the demonstration and/or the isolation of compounds capable of modulating or of inhibiting at least in part the interaction generally between the presenilin 1 or the presenilin 2 and the precursor of the β-amyloid peptide and/or the β-amyloid peptide particularly between the Aβ$_{1-42}$ peptide and the N-terminal end of PS2 is carried out according to the following steps:

- a molecule or a mixture containing different molecules is contacted with the Aβ$_{1-42}$ peptide synthesized with a biotin and an arm of 3 β-alanines (or of 3 lysines) at its N-terminal end (upstream of position 1)
- the above reaction mixture is incubated with the N-terminal end of a purified presenilin labelled with the aid of a first fluorophore. Advantageously, the fluophore is europium cryptate
- streptavidin (which will be immobilized on the biotin of the biot-Aβ$_{1-42}$ peptide) coupled to a second fluophore capable of being excited at the emission wavelength of the first fluophore is added such that it benefits from a fluorescence transfer if the two fluorophores are found in close proximity.
- the demonstration of the novel compounds inhibiting the interaction is detected by fluorometry at the emission wavelength of the first fluophore and/or by measuring the decrease in the signal at the emission wavelength of the second fluophore According to a particular embodiment, this second fluophore is XL665 which is allophycocyanin crosslinked chemically to increase its fluorescence at 665 nm (CisBiointernational). The loss of interaction is thus detected by fluorometery at the emission wavelength of the first fluophore and by the decrease in the signal of XL665 whose emission wavelength is at 665 nm.

This process is quite advantageous because it allows the interaction between the presenilins and the APP and/or the Aβ peptide in liquid and homogeneous phase to be demonstrated directly and consequently the inhibitory molecules of the said interaction to be demonstrated. In fact, this process is based on the transfer of fluorescence between two fluophores if these two chromophores are in physical proximity (thus in the case of interaction between Aβ$_{1-42}$ and the recombinant protein). According to a preferred variant of the process, the first fluorophore is europium cryptate, carried by the labelled recombinant protein (excited at 337 nm) reacting with the streptavidin-XL665 immobilized on the biot-Aβ peptide, and in particular the biot-Aβ$_{1-42}$ peptide. Advantageously, the labelled protein is formed by the N-terminal end of one or the other of the presenilins (PSNT-K). The loss of the fluorescence at 665 nm and the increase in the fluorescence at 620 nm characteristic of the europium cryptate indicates an inhibition of the interaction between the presenilins or their N-terminal ends and the APP and/or the Aβ peptide by the molecules sought.

According to a variant of this process, the molecule or the mixture containing the different molecules can be first contacted with the N-terminal end of a labelled purified presenilin with the aid of europium cryptate (PSNT-K) and then with the Aβ1-40 or Aβ1-42 peptide carrying a biotin and an arm of 3 β-alanines (or of 3 lysines) at their N-terminal end. The demonstration of novel molecules capable of modulating or of inhibiting at least in part the interaction between the presenilin 1 or the presenilin 2 and the precursor of the β-amyloid peptide and/or the β-amyloid peptide will be likewise made, after addition of the streptavidin labelled on the XL665, by spectrofluorometry according to the method above and in particular by reading of the fluorescence at 665 nm.

According to a last embodiment of the process of demonstrating compounds inhibiting the interaction generally between the presenilins (1 or 2) and the APP or the Aβ peptide and particularly between the Aβ$_{1-42}$ peptide and the N-terminal end of PS2 has the following steps:

- a mixture a) of cell lysates containing all or part of a presenilin (PS1 or PS2) and advantageously the N-terminal end, b) of cell lysates containing the APP, lysates obtained starting from cells infected by viruses and in particular by baculoviruses and c) the molecule or a mixture containing different molecules to be tested are contacted
- the proteins solubilized and corresponding to the presenilins or to the APP or the A βpeptide are co-immunoprecipitated with the aid of antibodies which are appropriate and well-known to the person skilled in the art
- the loss of the co-immunoprecipitation of the presenilins and of the APP is visualized by Western blot with marker antibodies indicating that the molecules tested have the sought inhibitory property In a particular embodiment, the processes of the invention described above are adapted to the demonstration and/or the isolation of ligands, agonists or antagonists of the interaction between the presenilins and the precursor of the β-amyloid peptide and/or the β-amyloid peptide.

The present invention likewise relates to the use of the polypeptides defined above for the demonstration of ligands of the polypeptides but above all of ligands of the presenilins, of the precursor of the β-amyloid peptide and/or of the β-amyloid peptide, and preferentially of the Aβ$_{1-42}$ peptide and/or of the N-terminal end of PS2, as well as of compounds capable of inhibiting at least in part the interaction between a presenilin and the precursor of the β-amyloid peptide and/or the β-amyloid peptide.

Another subject of the invention relates to the use of a ligand or of a modulator identified and/or obtained according to the processes described above as medicament. Such ligands or modulators by means of their capacity to interfere at the level of the interaction between the presenilins and the precursor of the β-amyloid peptide and/or the β-amyloid peptide can thus modulate the production of the amyloid peptide Aβ$_{1-42}$ and allow certain neurological disorders and especially Alzheimer's disease to be treated.

Another subject of the invention relates to the perfection of an interaction test between a presenilin and the precursor of the β-amyloid peptide and/or the β-amyloid peptide, and preferentially between the Aβ$_{1-42}$ peptide and the N-terminal end of PS2, characterized in that it comprises at least one fluorescence transfer step between two fluophores immobilized on the preceding molecules and a step of visualization of the interaction measured by spectrofluorometry. As mentioned above, this test is also used to demonstrate molecules which inhibit the said interaction, according to the method for detecting the inhibition of the interaction, described in the present application.

The invention additionally relates to any pharmaceutical composition comprising as active principle at least one polypeptide such as defined above.

It also relates to any pharmaceutical composition comprising as active principle at least one antibody or antibody fragment such as defined above, and/or an antisense oligonucleotide and/or a ligand such as defined above. The invention likewise relates to any pharmaceutical composition comprising as active principle at least one nucleotide sequence such as defined above.

In addition, it also relates to the pharmaceutical compositions in which the peptides, antibodies, ligands and nucleotide sequences defined above are associated with each other or with other active principles.

It likewise relates to the compositions in which the nucleotide sequences according to the invention are incorporated in a recombinant viral or non-viral vector.

The pharmaceutical compositions according to the invention can be used to inhibit at least in part the interaction between a presenilin and the precursor of the β-amyloid peptide and/or the β-amyloid peptide. They are more preferentially pharmaceutical compositions intended for the treatment of neurodegenerative diseases such as, for example, Alzheimer's disease.

Another subject of the present invention is the use of the polypeptides described previously to inhibit at least in part the interaction between a presenilin and the precursor of the β-amyloid peptide and/or the β-amyloid peptide and preferably the use of these polypeptides to obtain a medicament intended for the treatment of neurodegenerative diseases and especially of Alzheimer's disease.

For their use according to the present invention, the polypeptides of the invention on the one hand or any molecule capable of inhibiting at least in part the interaction between a presenilin and the precursor of the β-amyloid peptide and/or the β-amyloid peptide, the corresponding nucleic sequences on the other hand or additionally the vectors such as described above are preferentially associated with one or more pharmaceutically acceptable vehicles to be formulated with a view to administration by the topical, oral, parenteral, intranasal, intravenous, intramuscular, subcutaneous, intraocular or transdermal route, etc. Preferably, they are used in an oral form. The injectable form can nevertheless be envisaged and could in particular be formulated with sterile, isotonic saline solutions (monosodium or disodium phosphate, sodium, potassium, calcium or magnesium chloride, etc, or mixtures of such salts), or dry, especially lyophilized, compositions which, according to the case, allow the formation of injectable solutions by addition of sterilized water or of physiological serum.

The doses of vector and in particular of a virus used for the administration can be adapted as a function of different parameters, and especially as a function of the site of administration considered (organ, nervous or muscular tissue), of the number of injections, of the gene to be expressed, or even of the duration of the treatment sought. Generally, the recombinant adenoviruses according to the invention are formulated and administered in the form of doses of between $10^4$ and $10^{14}$ pfu, and preferably $10^6$ to $10^{10}$ pfu.

The term pfu ("plaque forming unit") corresponds to the infectious power of a virus solution, and is determined by infection of an appropriate cell culture, and measures, generally after 15 days, the number of plaques of infected cells. The techniques for the determination of the pfu titre of a viral solution are well documented in the literature.

The present invention offers an efficacious means for treating the diseases in which the interaction between a presenilin and the precursor of the β-amyloid peptide and/or the β-amyloid peptide is involved and preferably for the treatment of neurodegenerative diseases and especially of Alzheimer's disease.

The present invention will be more fully detailed with the aid of the examples below, which are considered as being of descriptive and non-limiting manner.

LIST OF THE FIGURES

FIG. 1: A) Scheme of the truncated PS2 constructs

B) Expression in COS1 cells.

Figure 2:
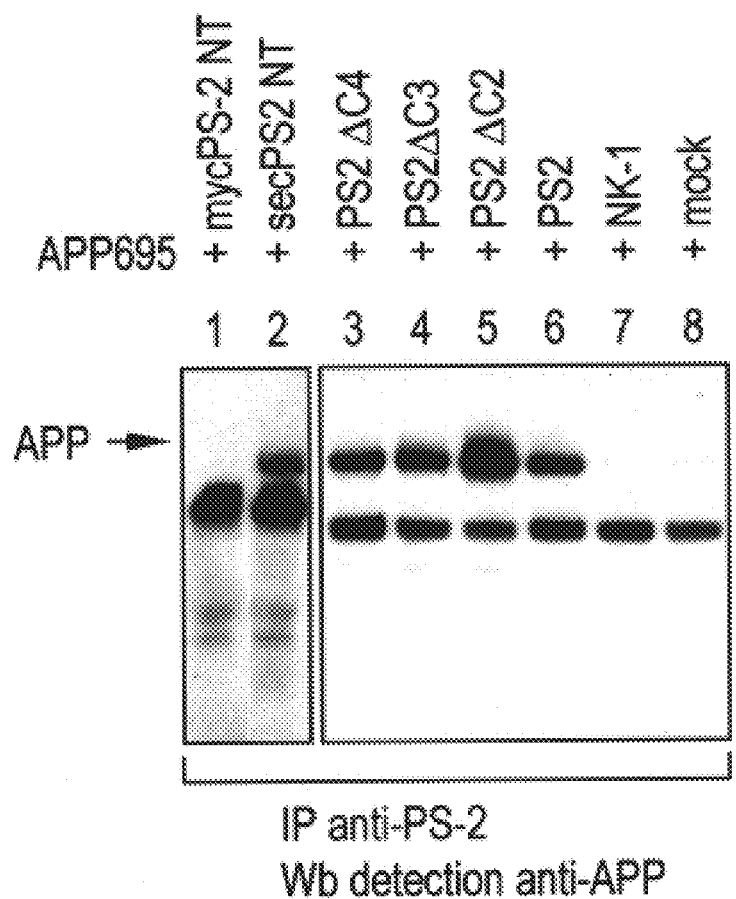

FIG. 2: Interaction of the truncated forms of PS2 with APP.

FIG. 3: A) Interaction of the secreted N-term of PS2 (§ecPS2T) and of extracellular APP.

B) Demonstration of the interaction SecPS2NT/APP but not of myc-PS2NT/APP in extracellular medium.

FIG. 4: Interaction of PS2 with the truncated forms of APP:

A) Interaction of PS2 with the SPA4CT form of the APP but not with the cytoplasmic domain of the APP (MC45F)

B) Interaction of PS2 with the C100 form of the APP

FIG. 5: Interaction of PS1 and PS1DC2 with APP and its short form:

A) Interaction of PS1 with the complete form of the APP and the truncated form SPA4CT B) Interaction of the truncated form of PS1 (PS1 ΔC2) with the APP FIG. 6: Interaction of PS1 and of APP in insect cells.

A) Anti-Histidine immunoprecipitates (label on PS1), APP visualization

B) Anti-PS1 immunoprecipitates, APP visualization

C) Inverse anti-APP immunoprecipitates, PS1 visualization

Figure 7:
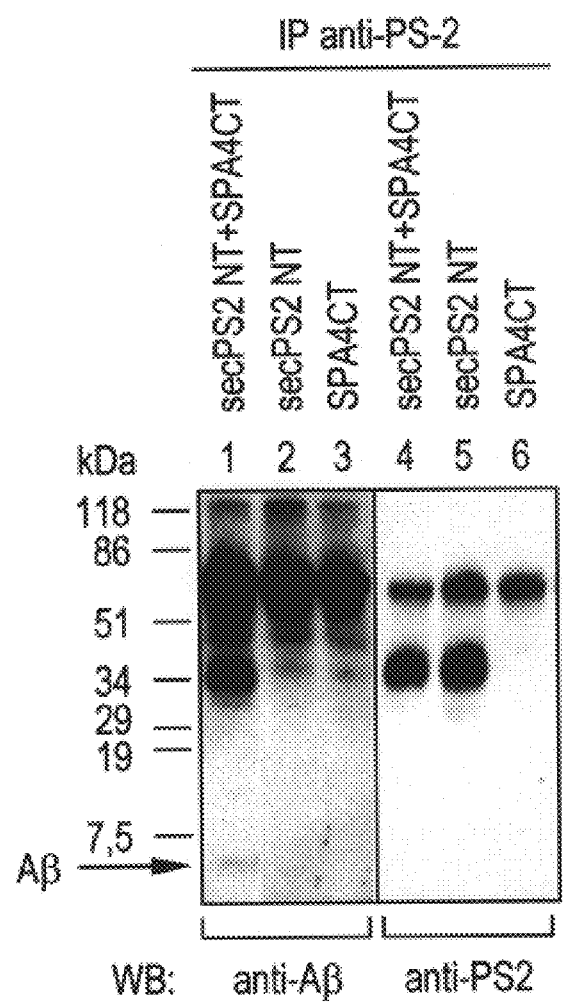

FIG. 7: Interaction of the secreted form of PS2NT with the Aβ peptide in the extracellular medium.

Figure 8A:
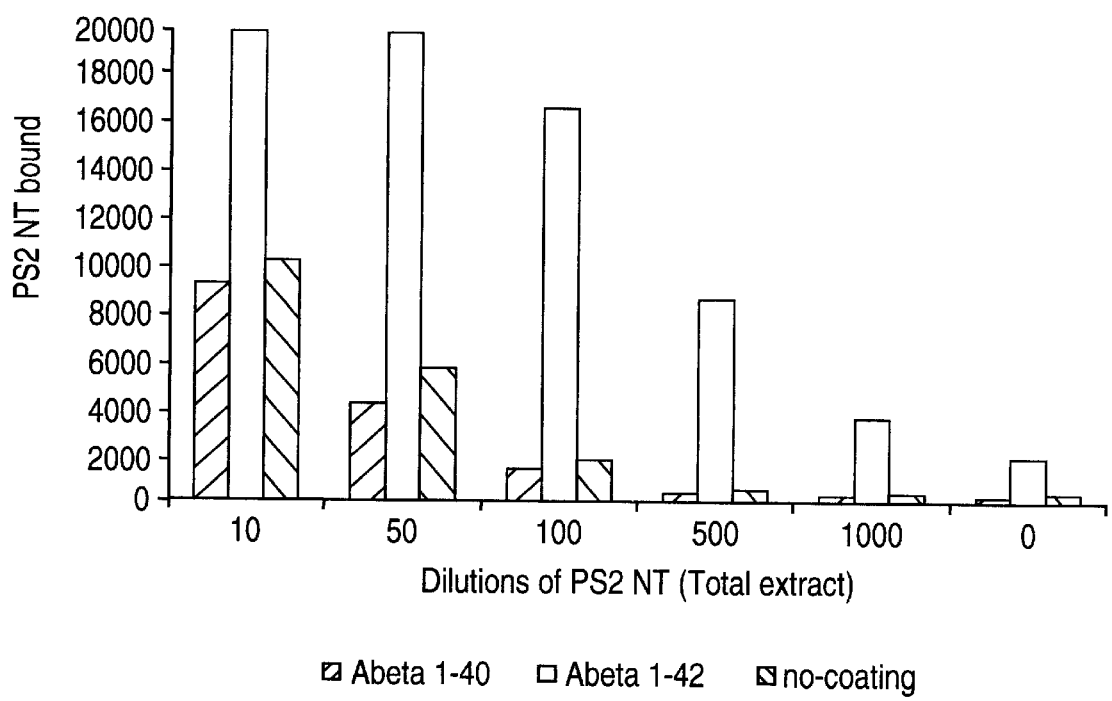
Figure 8B:
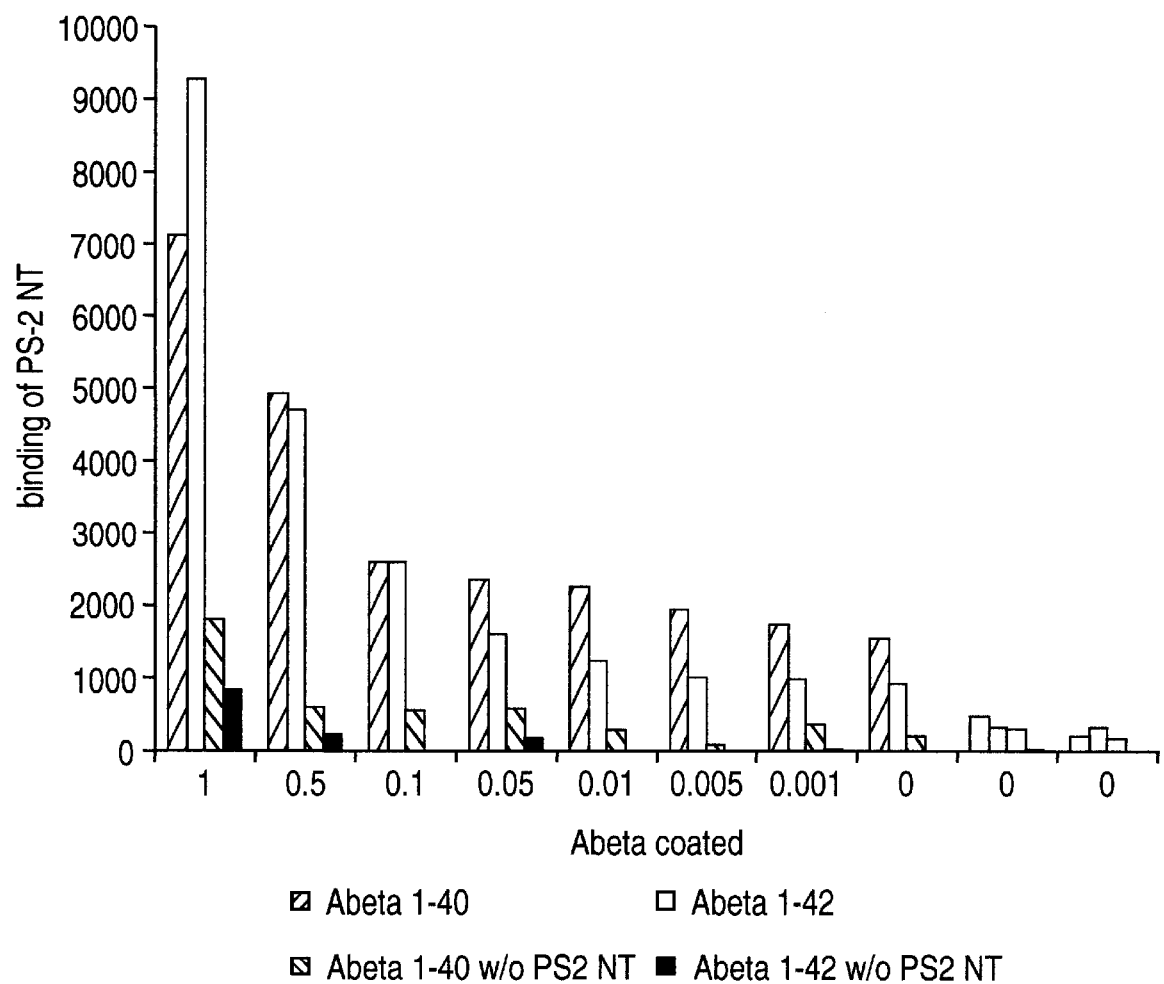

FIG. 8: Reconstitution of the AP/PS2Nt interaction in vitro on a nitrocellulose filter.

A) Dose-dependence as a function of the concentration of PS2Nt

B) Dose-dependence as a function of the concentration of A β.

FIG. 9: Interaction in vitro of the complete forms of PS1 and APP.

A) Anti-Histidine immunoprecipitates

B) Anti-PS1 immunoprecipitates

FIGS. 10A and 10B: Displacement by the N-terminal end of PS2 preceded by a signal peptide (SecPS2NT) of the interaction between PS1 and PA4CT of the interaction between PS1 and the SPA4CT fragment.

Figure 11:
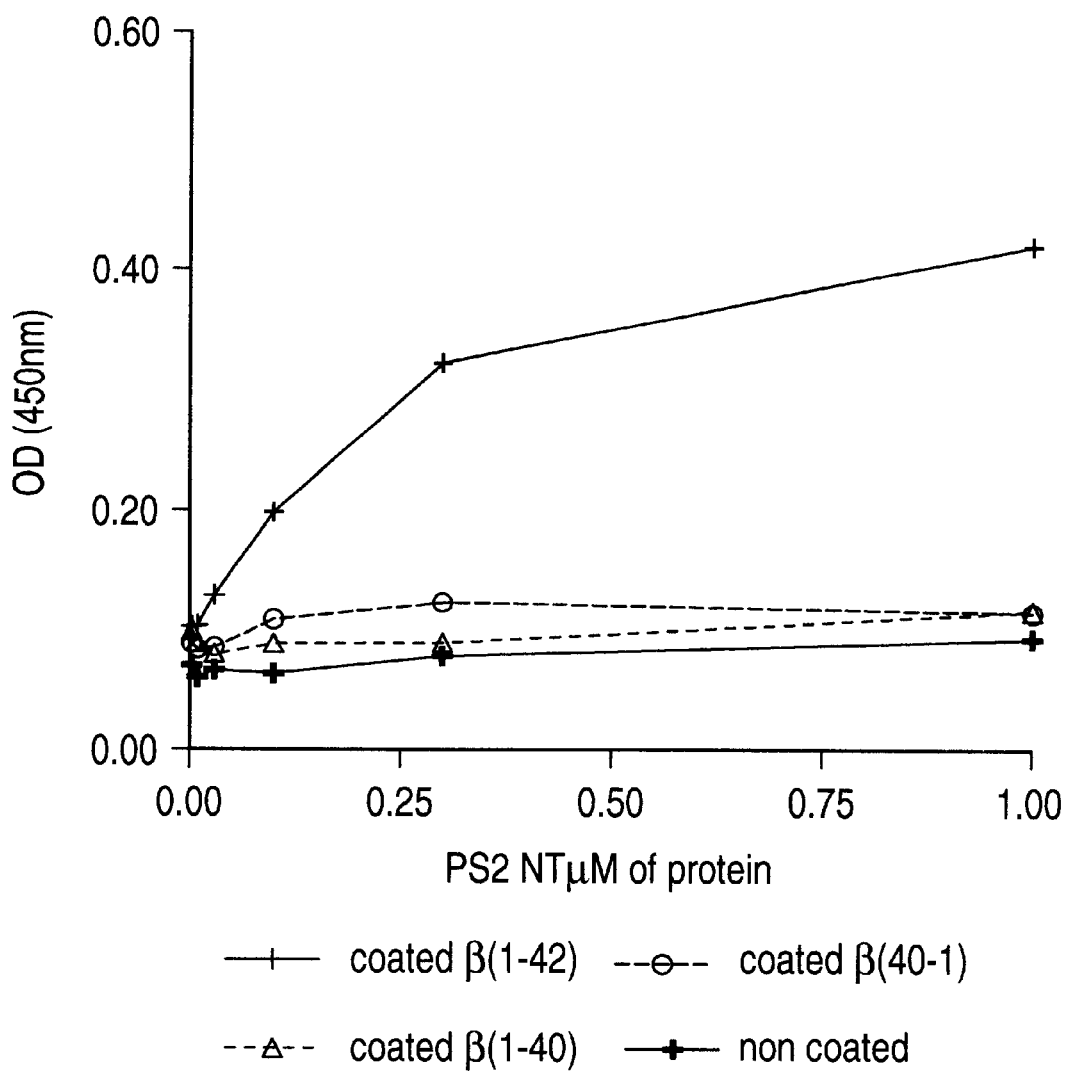

FIG. 11: Interaction of PS2 NT with the $Aβ_{1-42}$ peptide in vitro demonstrated by the 96-well plate test (ELISA)

Figure 12:
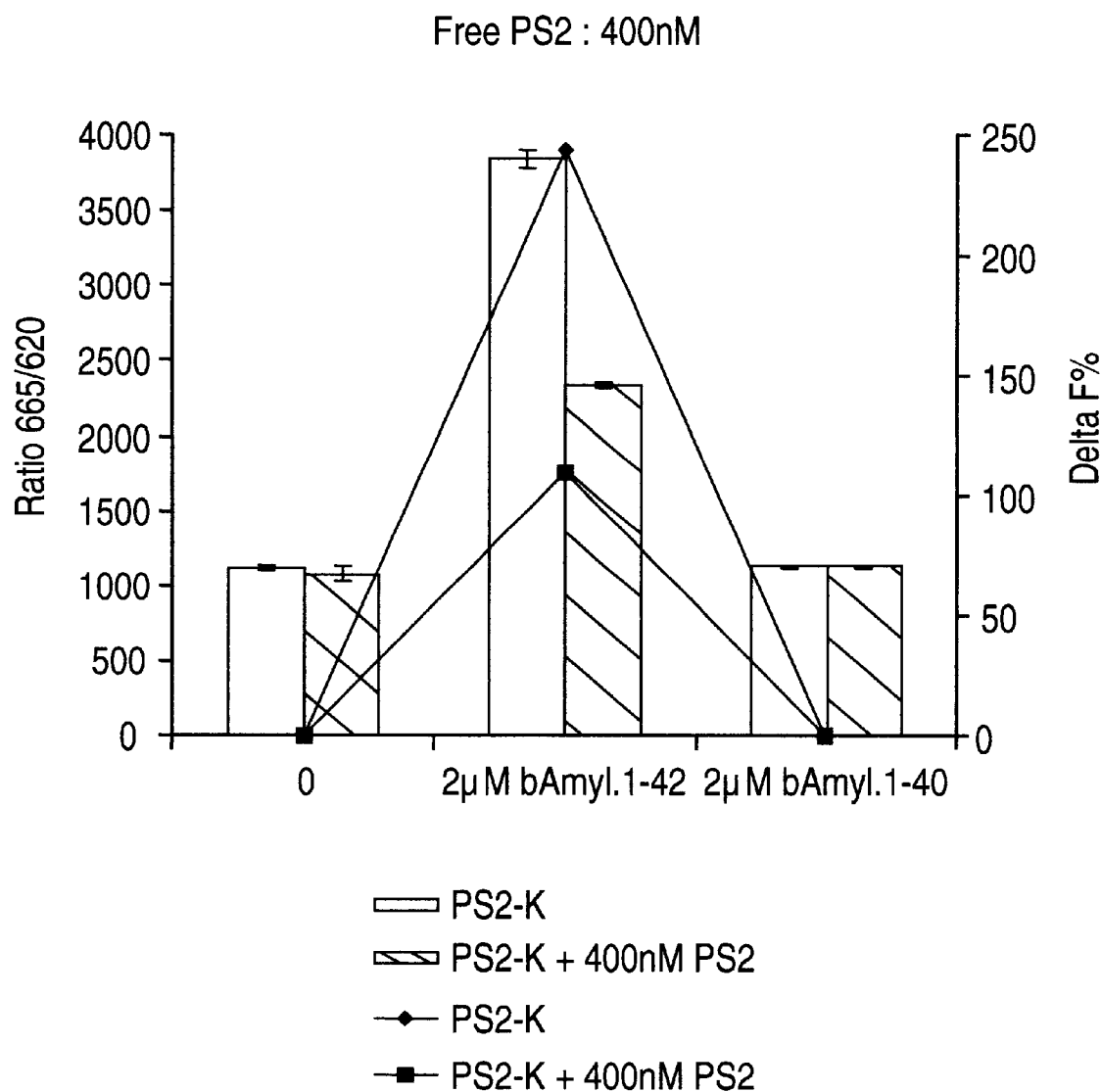

FIG. 12: Interaction of PS2 NT with the $Aβ_{1-42}$ peptide demonstrated by the HTRF (homogenous Time-Resolved Fluorescence) transfer test.

FIG. 13: The blocking of the APP/PS1 interaction with SecPS2NT leads to the inhibition of the production of intracellular $Aβ_{1-42}$ amyloid peptide A). Demonstration that the blocking of the APP/PS1 interaction with SecPS2NT leads to the inhibition of the production of intracellular $Aβ_{1-42}$ amyloid peptide B) Checking that the expression of SecPS2NT does not have any influence on the expression of different transgenes FIG. 14: Detection of the interaction of PS2 with the endogenous APP of COS cells with the aid of pharmacological treatment with lactacystine FIG. 15: Interaction of PS2 and PS2 NT with a second region of the APP, different from the Aβ peptide.

MATERIALS AND METHODS

A/MATERIALS

1. Constructs Expressing the Presenilins.

The obtainment of expression vector (host vector, pcDNA1, INVITROGEN in mammalian cells of human proteins PS1 and PS2 has already been described (Pradier et al., 1996). Several successive deletions on the C-terminal end of PS2 were generated see FIG. 1A). The numbering was carried out starting from the initiation codon of PS2 as position 1.

The restriction fragment HindIII of the vector PS2 (of the 5' non-coding, position −55, in the internal site at position 1080) was purified and ligated with the vector pcDNA3 linearized with HindIII and treated with alkaline phosphatase. The truncated PS2 thus produced (PS2ΔC1) extends from the N-terminal end to the residue 361 plus 7 residues supplied by the 3' end and thus comprises the first six transmembrane domains and a large part of the hydrophilic loop (FIG. 1A).

PS2ΔC2 was constructed by digestion of the plasmid PS2 by PstI (internal site at position 679) and ligation with the fragment PstI corresponding to the 3' non-coding part of the vector PS2. The truncated protein PS2ΔC2 extends from position 1 to the residue 228 of PS2 plus 18 additional residues supplied by the 3' end. It includes the four first transmembrane domains of PS2.

A similar construct was carried out for PS2 carrying the mutation H141I,PS2ΔC2*.

The restriction fragment HindIII (−55)/MscI(590) of the construct PS2ΔC2 was then cloned into the vector pcDNA3 treated by HindIII and whose ApaI end was rendered blunt-ended. This PS2ΔC3 construct extends from the N-term end to the residue 198 plus 2 additional residues thus comprising the first three transmembrane domains of PS2.

The restriction fragment of PS2ΔC2, HindIII (−55)/NcoI (504) rendered blunt-ended at its NcoI end by treatment with the Klenow fragment of the DNA polymerase was recloned in the same vector pcDNA3 HindIII/(blunt-ended ApaI) to construct PS2ΔC4 extending up to the residue 168 of PS2 plus 3 additional residues.

The construct of the N-terminal hydrophilic end of PS2 was obtained by amplification of the sequence PS2 with the oligonucleotides ext5':

5'-CG GAATTCATCGATTCCACCATGCTCACATTCAT GGCC-3' (SEQ ID NO:7 (overlapping the initial ATG, in bold, and introducing an EcoRI restriction site, underlined) and ext3':

5'-CCG CTCGAGTCATTGTCGACCATGCTTCGCTCCGT ATTTGAGG-3' (SEQ ID NO:8 (introducing a stop codon after the residue 90 of PS2 as well as an XhoI restriction site, underlined).

After cloning in the vector pCRII by the TA cloning method (INVITROGEN), the conformity of the PCR fragment was verified by sequencing. This fragment, (EcoRI/XoI) was then introduced into a pcDNA3 vector in phase with a sequence corresponding to the myc epitope at its N-terminal end: mycPS2Nter.

In order not to prejudge the topology of PS2, the same Nter fragment was recloned in the pSectagB vector, in phase with the sequence of the signal peptide of IgkB to direct the secretion of the protein pS2Nter:SecPS2-Nter.

The C-term end of PS2 was constructed in a similar manner with the aid of the restriction fragment HindIII (1080)/PstI(in 3' non-coding) recloned in the vector pSec-TagB HindIII/PstI, SecPS2Cter extending from the residue 361 to the C-terminal end, or in the vector pcDNA3myc in phase with the myc epitope.

In the same way, a truncated construct of PS1 was obtained. The vector pcDNA3-PS1 was digested by PflmI (site in position 636 of the coding nucleic sequence of PS1) and XhoI in the 3' non-coding of the sequence of PS1. These sites were converted into blunt-ended form by treatment with T4 DNA polymerase. The vector fragment, purified on agarose gel, was religated to itself to provide an expression vector of a truncated PS1 extending from the N-ter of PS1 up to residue Ile213 (after the 5th transmembrane domain) plus 12 additional residues. This construct corresponds to chimeric ΔC2 and is called PS1ΔC2.

2. Constructs Expressing APP.

2.1 APP Constructs

The different full APP constructs (isoform 695) and SPA4CT (the last 100 residues of APP (amino acid 597 to 695) preceded by a signal peptide for insertion into the membrane) have already been described (Dyrks et al., 1993). The vectors, for the expression of C100 and of the cytoplasmic domain of APP, were obtained in the following manner: the corresponding cDNAs were obtained by enzymatic amplification of the DNA (PCR (polymerase chain reaction)) using, as synthesis primer, the following oligonucleotides: for C100: the oligonucleotides 8172 and 8181; for the cytoplasmic domain of APP: the oligonucleotides 8171 and 8181.

Oligo 8172 5' CAAAGATCTGATGCAGAATTCCGACAT 3' (SEQ ID NO:9), containing:

- a recognition site for the restriction enzyme BglII (underlined)
- the coding sequence for the amino acids 597–602 of APP (in bold) [APP numbering of 695 amino acids]

Oligo 8181 5' CAA GCGGCCGCTCATCCCTTGTCATCGTCGTCCT TGTAGTCTCCGTTCTGCATCTGCTC 3' (SEQ ID NO:10) containing:

- a recognition site for the restriction enzyme NotI (underlined)
- the complementary sequence to the sequence coding for the amino acids 691–695 of APP (in bold) [APP numbering of 695 amino acids]
- the complementary sequence to the sequence Asp-Tyr-Asp-Asp-Asp-Asp-Lys corresponding to the FLAG epitope (in italics).

Oligo 8171 5' CAAAGATCTAAGAAACAGTACACATCC 3' (SEQ ID NO:11), containing:

- a recognition site for the restriction enzyme BglII (underlined)
- the sequence coding for the amino acids 650–655 of APP (in bold) [APP numbering of 695 amino acids]

The enzymatic amplification products of the DNA were cloned in the vector pCRII. The nucleotide sequence was verified by the method of specific DNA terminators.

The cDNAs are then introduced by ligation into the expression plasmid derived from the plasmid pSV2 and containing, in the same reading frame, an MYC epitope.

2.2. Construction of the Soluble Forms of APP:α-sAPP and β-sAPP.

The cDNAs corresponding to the secreted forms of APP terminating at the α- and Δ-cleavage sites were obtained by PCR.

Oligonucleotide 1:

5'-ccatcgatggctaCATCTTCACTTCAGAG-3' (SEQ ID NO:12) introduces:
a stop codon (underlined inverse complementary sequence) after position 1788 of APP corresponding to the Δ cleavage site.
and a ClaI restriction site.

Oligonucleotide 2:

5'-ccatcgatggctaTTTTTGATGATGAACTTC-3' (SEQ ID NO:13) introduces:
a stop codon (underlined inverse complementary sequence) after position 1836 of APP corresponding to the α cleavage site.
and a ClaI restriction site.

Oligonucleotide 3:

5'-CCGTGGAGCTCCTCCCG-3' (SEQ ID NO:14), common to the two forms, corresponds to the region 1583 to 1600 of the APP including the internal restriction site of the APP SacI (underlined).

The cDNA of the APP was amplified by PCR using oligo3-oligo1 and oligo3-oligo2 pairs for β-sAPP and α-sAPP respectively. The amplification products were subcloned as previously in PCRII and the sequences verified by sequencing. For each, the restriction fragment SacI-ClaI was purified and recloned in the expression vector APP (see above) itself digested by SacI-ClaI to replace the C-terminal part of the APP by the C-terminal fragments of β-sAPP and α-sAPP respectively and to reform the complete proteins.

3. Baculovirus Constructs.

The obtainment of transfer vector for baculovirus coding for the human protein PS1 was carried out starting from the expression vector for mammalian cells (Pradier et al., 1996). The cDNA coding for the protein PS1 was extracted by a digestion with the restriction enzymes XhoI and NotI, then cloned in the transfer plasmid pAcHTLB (6-Histidines fusion protein) and pAcSG2 (native protein). The obtainment of recombinant baculoviruses is carried out according to the protocol of the supplier (PHARMINGEN) and consists in cotransfecting $2 \times 10^6$ insect cells (sf9) with 1 µg of transfer plasmid containing the gene of interest and 0.5 µg of viral DNA (BACULOGOLD). After 5 days at 27° C., the cells are removed by scraping, then centrifuged, the supernatant is used as viral stock for the amplification and the determination of the viral titre, the expression of the protein is visualised by Western blot on the cell pellet.

The obtainment of the baculovirus expressing human APP (695) has been described previously (Essalmani et al., 1996).

For the study of the expression of PS1 and of APP, the sf9 cells are coinfected with an M.O.I. of 2 by baculoviruses expressing the human APP (695), the human protein presenilin 1 (PS1), or PS1 with a tag 6 histidine at the N end (6HisPS1), or the control protein of pseudomas putrida XylE with a tag 6 histidine at the N end (6HisXylE), then solubilized with a 10 mM Tris buffer, 130 mM NaCl, 1% Triton X100, 1% NP 40, pH 7.5.

The solubilized proteins are immunoprecipitated by an antihistidine antibody (A), antiPS1 (1805)(B), or antiAPP (22C11)(C). The presence of the APP or of PS1 was revealed by Western blot with the antibody antiAPP aCT43(A), 22C11(B), or the antibody antiPS1 95/23(C).

The solubilized fractions containing the APP, PS1 or 6HisPS1 are mixed, then immunoprecipitated in the presence of antihistidine antibodies or antiPS1 for one night at 4° C. The coimmunoprecipitation of the APP is revealed after Western blot with the antibodies αCT43 or 22C11.

4. The Plasmids

The plasmids used for the invention are the following:

pcDNA is a commercial plasmid (INVITROGEN) used for cloning and expression in mammalian cells of the sequences PS1 and PS2 and of their truncated forms.

pCRII is a commercial plasmid (INVITROGEN), used for the cloning of PCR fragments.

pSecTagB is a commercial plasmid (INVITROGEN), used for cloning and expression in mammalian cells of cDNA to which are added the secretion signal (Igκ signal peptide).

pSV2 is a commercial plasmid (PHARMACIA), used for cloning and expression in mammalian cells of cDNA.

pAcHTLB is a commercial plasmid (PHARMINGEN), for the insertion of a (His)6 epitope into cDNAs and homologous recombination with baculoviruses.

pAcSG2 is a commercial plasmid (PHARMINGEN), for homologous recombination with baculoviruses.

pET29a is a commercial plasmid (NOVAGENE), for the expression of cDNA in bacteria.

B/METHODS

1. Transfection of cells

The method established for COS1 cells or CHO cells consists in utilizing a lipofectant in a ratio of 1 to 8 (weight/weight) with respect to the DNA and an H1 synthetic peptide (sequence: KTPKKAKKPKTPKKAKKP (SEQ ID NO:15)) in the same ratio in order to optimize the compaction of the DNA and the efficacy of transfection. This method is based especially on the neutralization of the charges of the phosphates of the DNA by the positive charges of the lipofectant.

The COS1 cells are cultured in an incubator at 37° C., 95% humidity and 5% $CO_2$ in DMEM medium (Dulbecco's Modified Eagle's Medium) containing 4.5 g/l of glucose (GIBCO-BRL) supplemented with 3% of L-glutamine, 1% of penicillin-streptomycin and 10% of foetal calf serum.

The day before transfection, the cells are inoculated at a density of 2.5 $10^6$ cells per 100 mm dish. On the day of transfection, the cells are rinsed twice with PBS (phosphate buffer saline) and once in OPTIMEM (patented composition; GIBCO-BRL) for a habituation of at least 15 minutes in an incubator.

In an equivalent 100 mm dish, 8 µg of plasmid DNA in total are added to 300 µl of OPTIMEM and 64 µg of H1 peptide. After having vortexed vigorously for 10 seconds, there is a waiting period of 5 minutes and lipofectamine (32 µl, or 64 µg) diluted in 300 µl of OPTIMEM is added to the preceding mixture. The whole is vortexed vigorously a further time and then allowed to stand for 30 minutes. Five millilitres of OPTIMEM are added by tube and the vortexed mixture is placed on the cells (from which the medium has previously been aspirated). The cells are then placed in an incubator for 4 hours, at the end of which the mixture is replaced by complete medium.

2. Lysis of the Cells and Determination of the Proteins

The cells are most often lysed 48 hours after transfection (at the usual expression maximum).

The lysis buffer contains 10 mM of Tris pH 7.5, 1 mM of EDTA, 1% of TRITON X100, 1% of NP40 and a cocktail of protease inhibitors (COMPLETE[8], BOEHRINGER MANNHEIM). For each plaque, after rinsing with PBS, 800 µl of the cold buffer are added. The lysates then undergo sonication followed by stirring with a magnetic bar at 4° C.

for one night. Centrifugation for 30 minutes at 15,000 rpm separates the pellet from the supernatant. The soluble proteins are then determined according to the BCA kit (PIERCE) in order to be able to standardize the following experiments.

3. Immunoprecipitations

The antibodies directed against the peptide of the N-term of PS2, 95041, (Blanchard et al., 1997) and against the twenty first amino acids of PS1 (Duff et al., 1996) were obtained in rabbits by immunization with synthetic peptides. For immunoprecipitation, 100 μg of proteins are diluted in 400 μl of modified RIPA (150 mM NaCl, 50 mM Tris pH 8.0, 1% TRITON X100 v/v, 1% NP40 v/v). Thirty microlitres of protein A Sepharose suspension (0.1% m/v in PBS solution) and 3 μl of antibody are added. The suspensions are gently mixed on a rotating shaker at 4° C. for one night. The protein A Sepharose complex is washed 3 times with 0.5 ml of modified RIPA and once with 0.5 ml of "Wash C" washing buffer (10 mM Tris pH 7.5).

4. Immunotransfer

The samples are deposited on Tris-glycine gels (NOVEX), with a different percentage of acrylamide according to the molecular weight to be discriminated. A molecular weight marker is likewise deposited (BROAD RANGE, BIORAD). Migration takes place for approximately 2 hours at 100 volts constant in SDS 1 X final buffer (NOVEX). The gel is then transferred to a nitrocellulose or PVDF membrane (1X final transfer buffer (NOVEX) with 10% of methanol) for 2 hours at 150 mA constant.

After transfer, the membrane is blocked for 2 hours at ambient temperature in 50 ml of PBS-T (PBS with 0.5% Tween) containing 2% of skimmed milk (MERCK). The primary antibody (diluted to the optimal concentration of the order of 1/1000th to 1/5000th, in PBS-T with or without 2% of skimmed milk) is left for one night at 4° C. After brief rinsing in PBS-T, the membrane is incubated for 45 minutes in the presence of the second antibody (anti-mouse or anti-rabbit IgG according to the case, coupled to Raifort peroxidase) diluted to 1/5000th in a buffer called "ECL" (Tris 20 mM, NaCl 150 mM, Tween 0.1%).

The membrane is then rinsed 4 times for 15 minutes in "ECL" buffer. It can be visualised by the ECL reagent (AMERSHAM) formed of 2 buffers to be mixed for immediate use in an equal volume. Different exposures of a photographic film (HYPERFILM ECL; AMERSHAM) are carried out, followed by development.

5. In Vitro Immobilization of PS2 NT With the Aβ-amyloid Peptide 5.1 Production of the Recombinant Protein PS2 NT in Bacterium.

For the creation of a bacterial expression vector of PS2NT (amino acids 1 to 87), the cDNA of PS2 was amplified by PCR with the oligonucleotides 3': (CCGCTCGAGTCATTGTCGACCATGCTTCGCTCCG TATTTGAGG) (SEQ ID NO:8) and 5'(CCGGAATTCATCGATTCCACCATGCTCACATTC ATGGCC) (SEQ ID NO:7). The resulting fragment was cloned in pCRII and the sequence confirmed. This fragment was then sub-cloned in the vector pET29a (NOVAGENE) in phase with the sequence of the S-tag label. The protein was produced in BL21 bacterium. After induction in IPTG for 5 h, the bacteria were recovered by centrifugation (10 min at 6000 rpm) and the cell pellet was dissolved in RIPA buffer (volume calculated by multiplying the OD of the culture after induction by the volume of culture divided by 23). The bacteria were lysed by sonication and the lysate was centrifuged at 13,000 rpm for 20 min at 4° C. The supernatant (total extract) was used for the immobilization studies.

The recombinant protein PS2NT has also been purified from the total extract on a Nickel column (poly-His label carried in the pET29a vector) as described by the supplier (NOVAGENE).

5.2 PS2NT/Aβ42 Immobilization Test on Nitrocellulose Membrane

The synthetic Aβ peptide (in solution) was deposited on nitrocellulose membrane (Schleicher and Schuell) using a 96 well dot-blot apparatus. After deposition, the filter was blocked (with regard to the non-specific sites of protein immobilization) with the blocking reagent gelatin (Novagen) diluted to a 10th in TBST. After blocking, the filter was replaced in the dot-blot apparatus and the PS2NT bacterial extract was added to the wells for an incubation of 2 h at ambient temperature. As control, a bacterial extract containing the empty plasmid pET29 was used in the wells in duplicate. The filter was then washed once with RIPA buffer, then withdrawn from the apparatus and washed three times with PBST (15 min for each wash). The detection of the S-tag label was then carried out as prescribed by the supplier (NOVAGEN) with a calorimetric substrate. Quantification of the calorimetric reaction (precipitate) was carried out by optical scanning of the filter and quantification of the intensity in each well by the computer program TINA 2.1 (RAYTEST).

5.3 PS2NT/Aβ42 Interaction Test in ELISA Format

The synthetic Aβ peptide (1-40 and 1-42) (100 ml, 2 mg/ml) is incubated overnight in 96-well plates for immobilization on the plastic. The plates are rinsed twice with PBS and the non-specific immobilization sites are saturated by incubation with 5% (w/v) of bovine serum albumin in PBS. The purified recombinant protein (according to the protocol described in 5.1), PS2NT, diluted in buffer (25 mM Tris/HCl, pH 7.5, 0.5% Triton X-100, 0.5% NP40) is added and incubated for 4 h at ambient temperature. After two rinses in PBS-Tween 0.5%, the PS2NT protein retained on the plate (interacting with the Aβ peptide) is visualized by incubation with the immobilizing protein of the S-tag coupled to alkaline phosphatase as above. The detection of the signal is carried out in a spectrophotometer at 450 nm.

5.4 PS2NT/Aβ1-42 Interaction Test in HTRF Format (Homogeneous Time-Resolved Fluorescence).

The purified PS2NT protein (produced according to the protocol described in 5.1) was labelled with the aid of the europium cryptate fluorophore (PS2NT-K). The $Aβ_{1-42}$ and $Aβ_{1-42}$ peptides were synthesized with a biotin and a spacer arm of 3 β-alanines (or of 3 lysines) at their N-terminal end (upstream of position 1 of the Aβ peptides) and two arginines (R) in their C-terminal end to facilitate the synthesis, biot-3K-Aβ40$_{RR}$ and biot-3K-Aβ42$_{RR}$ peptides.

The interaction reaction of PS2NT-K with biot-Aβ40 or biot-Aβ42 is carried out in a 10 mM HEPES buffer, pH=7.2, containing 150 mM NaCl, 3.4 mM EDTA and 3 mM CHAPS (detergent). The labelled PS2NT protein (final conc. 6 nM, i.e. 40 ml of initial solution at 15 nM) is incubated with the biot-Aβ40 or biot-βP42 peptide (final conc. 2 mM, i.e. 40 ml of initial solution at 5 μM and 20 μl of buffer) for 10 min followed by the addition of streptavidin labelled with the XL665 (XL665 is a crosslinked allophycocyanin, CIS-BIO INTERNATIONAL at a concentration of 8 μg/ml (i.e. 100 μl of initial solution at 16 μg/ml) in a 100 mM HEPES buffer pH=7.0 containing 400 mM KF, 133 mM EDTA and 1 g/l BSA. The reaction is incubated, and the plates are read on a PACKARD DISCOVERY counter which measures on the one hand the emission of the europium cryptate at 620 nm after excitation at 337 nm and on the other and the emission of the XL665 at 665 nm after fluorescence transfer at 620 nm by the europium cryptate on the XL665. The formation of the XL665-streptavidin/biot-Aβ42/PS2NT-cryptate complex leads to a fluorescence transfer of the cryptate to the XL665 which is measured at 665 nm by the counter. In the absence of formation of an XL665-streptavidin/biot-Aβ/PS2NT-cryptate complex, the Europium cryptate fluoresces at 620 nm.

EXAMPLES

Example 1

Interaction Between APP and PS2 and Mapping of the Interaction Zone on PS2

This example has the aim of determining the zone of interaction on PS2 and of demonstrating an interaction between the said region and the APP.

Figure 1B:
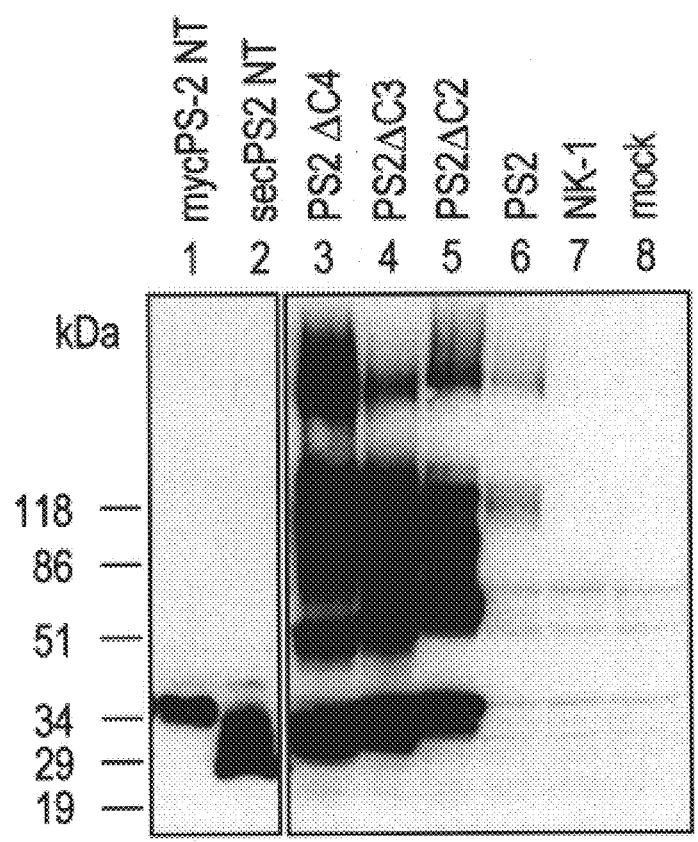

The interaction between the proteins APP and PS2 in mammalian cells is exemplified in FIG. 2. The lysate of transfected COS cells with PS2 and APP is subjected to immunoprecipitation with an antibody directed against the N-term of PS2 (95041, Blanchard et al., 1997). The immunoprecipitate is then analysed by immunotransfer with an antibody against the APP. The APP is clearly detected in the immunoprecipitates of the cells cotransfected with APP and PS2 but not in the absence of PS2 (FIG. 2, track 6 with respect to lane 7) as described above (Weidemann et al., 1997). To map the zone of interaction between these two proteins, several truncated forms of PS2 were constructed. In order to conserve the membrane topology of PS2 in general determined by the N-term part of the membrane proteins, progressive truncations of the C-term end of PS2 were produced terminating after different transmembrane domains TM6 (PS2ΔC1), TM4 (PS2ΔC2), TM3 (PS2ΔC3) and TM2 (PS2ΔC4), scheme FIG. 1A. The hydrophilic N-term end (87 residues) of PS2 was also constructed in cytoplasmic form (native sequence) or in secreted form by the insertion of the signal peptide of the Igk chain. The expression of these different forms is exemplified in FIG. 1B, revealed with the aid of the antibody anti-PS2 (95041). The constructs possessing hydrophobic domains additionally have bands corresponding to the monomeric forms at the expected molecular weights (here forming closely related doublets), dimeric forms and typical high molecular weight aggregates of PS2 (FIG. 1B, lanes 3–5). In particular for complete PS2, only these aggregates are detectable in this figure whereas the monomeric form is not detectable (lane 6). The two constructs of the hydrophilic N-term of PS2: mycPS2Nt and SecPS2Nt give rise to the bands at the expected molecular weights (FIG. 1B, lanes 1 and 2.). The construct SecPS2Nt is likewise secreted into the extracellular medium (FIG. 3B, lane 2) whereas the construct mycPS2Nt is, itself, cytoplasmic.

These constructs were cotransfected individually with the APP. The detergent-soluble fraction of the cell lysates was immunoprecipitated with the antibody directed against the N-term of PS2 and these immunoprecipitates were analysed by immunoblots. As with the complete PS2, the APP is detectable in the immunoprecipitates with all the truncated forms of PS2, PS2ΔC2 to PS2ΔC4 (FIG. 2, lanes 3–5) demonstrating the interaction between APP and the forms containing the N-term of PS2. This interaction with the APP is conserved with the N-term construct of PS2 in its secreted form (FIG. 2, lane 2) demonstrating that the anchorage of PS2Nt in the lipid membrane is not necessary for this interaction. On the contrary, the cytoplasmic form mycPS2NT does not interact with APP (FIG. 2, lane 1).

The reverse immunoprecipitation experiment with an anti-APP antibody and of the detection by the N-term antibody of PS2 has allowed the interaction between the APP and SecPS2Nt to be confirmed under different experimental conditions.

Figure 3B:
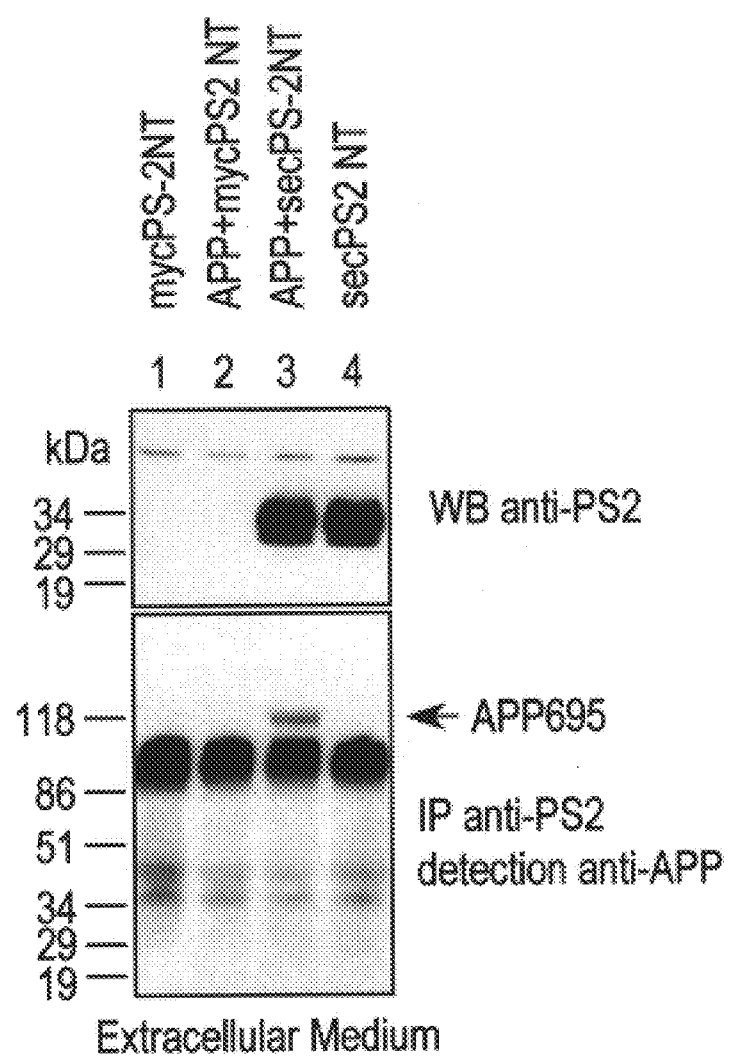

In the culture medium of cells cotransfected with APP and SecPS2Nt, an interaction between these two proteins is likewise demonstrated by coimmuno-precipitation (FIG. 3A, lane 4 and FIG. 3B, lane 3). The mycPS2NT form does not interact with APP in the medium (FIG. 3B, lane 2). The presence of this interaction in the medium demonstrates that the APP/PS2Nt complex is relatively stable in the course of the secretion process.

Example 2

Interaction Between APP and PS2 and Mapping of the Interaction Zone on APP.

This example has the aim of determining the zone of interaction in this on the APP and of demonstrating an interaction between the said region and the presenilin 2.

Figure 4A:
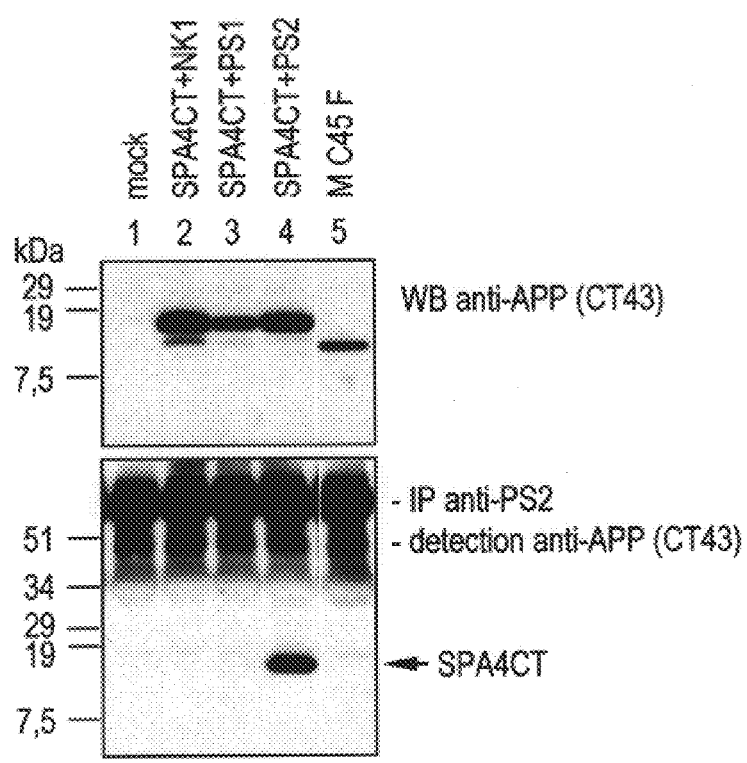

To this end, truncated forms of APP were used to delimit the zone of interaction on the APP. A construct containing the 100 last residues of the APP under the control or not under the control of a secretion peptide (SPA4CT and C100, Dyrks et al., 1993) and a construct containing only the cytoplasmic domain (the 45 last residues of the APP) were used and their presence was detected with the aid of an antibody directed against the cytoplasmic domain of the APP (αCT43, Stephens and Austen, 1996). In the cells cotransfected with PS2, it was possible to demonstrate an interaction of SPA4CT but not of the cytoplasmic domain of the APP with PS2 (FIG. 4A, compare lanes 4 and 5). It was also possible to demonstrate the interaction of PS2 with the construct C100 (without secretion signal) (FIG. 4B, lane 7). Even by combining the cytoplasmic domain of the APP with the membrane in a chimeric construction with the alpha receptor of the IL2, it was not possible to observe any interaction with PS2. This example demonstrates that an interaction exists with SPA4CT (residues 597 to 695 of the APP) but not with the cytoplasmic domain (residues 651 to 695) thus indicating that on the APP, the region of the Aβ (residues 597 to 637) and the remainder of the transmembrane segment (up to residue 650) are sufficient for the interaction with PS2.

Example 3

Interaction of PS1 With APP and Initial Mapping

This example has the aim of determining the zone of interaction on PS1 and of validating the interaction between the said region and the APP.

Figure 5A:
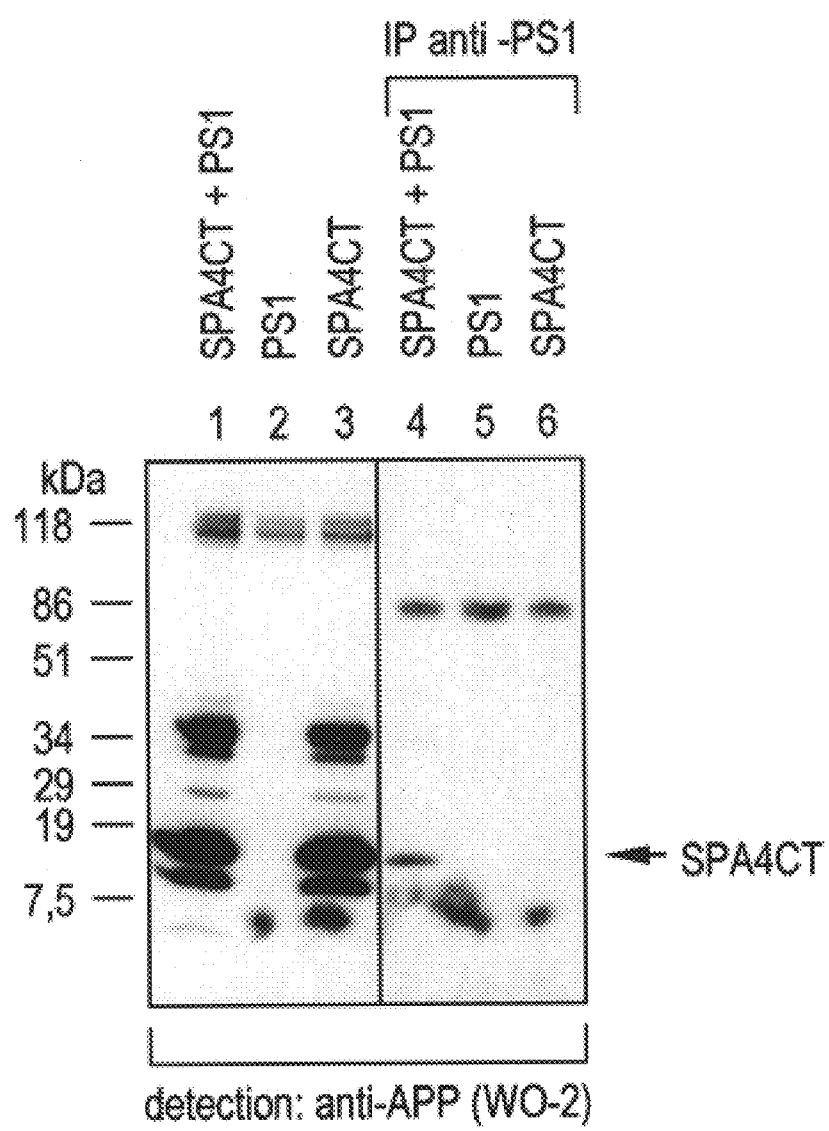
Figure 5B:
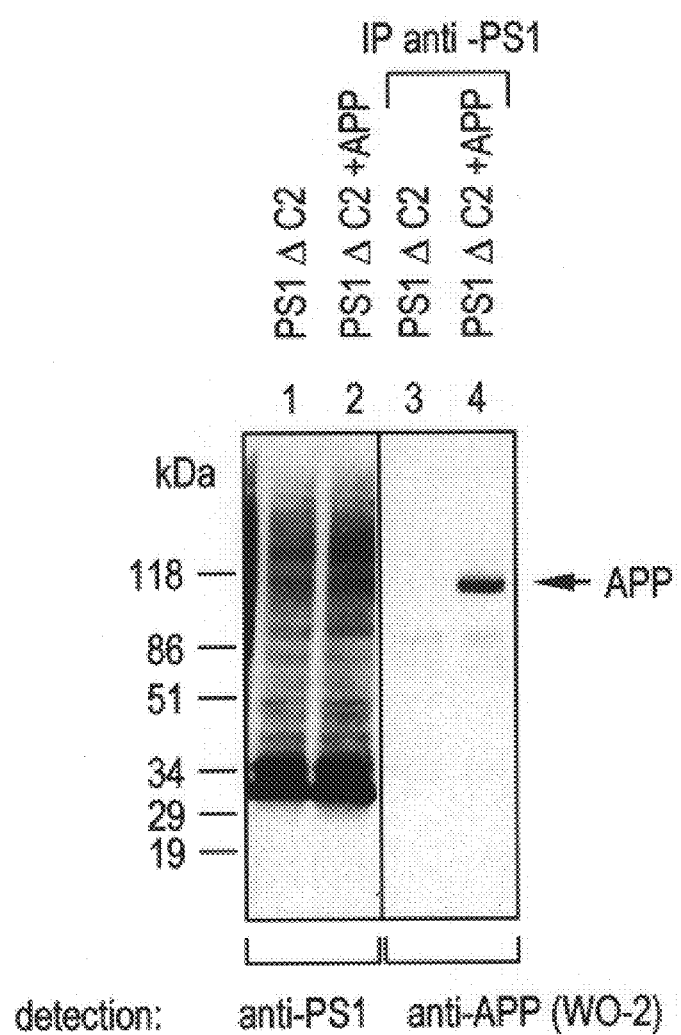

By analogy with the results obtained for PS2 (Examples 1 and 2), the study of the interaction of PS1 with APP was carried out in the same COS1 cell system. After coimmunoprecipitation with an antibody directed against the 20 last amino acids of PS1 (Duff et al., 1996), the SPA4CT, the C-terminal fragment of the APP, can be detected in the precipitates (FIG. 5A, lane 4). The APP also interacts with PS1. In the same way, the truncated form of PS1, PS1ΔC2 (1-213), interacts with APP (FIG. 5B. lane 4). These first data allow us to envisage that the regions of interaction between APP and PS1 may be closely related to those exemplified above with PS2.

To verify the validity and the generality of this PS1/APP interaction, a different cell system was used, in which the insect cells were infected by recombinant baculoviruses expressing the PS1 with or without His6 label and the APP (cf. Materials and methods). The study of the cell lysates allowed APP to be detected in the antiHis6 immunoprecipitates (for PS1-His6, FIG. 6A, lane 4) or antiPS1 (for PS1 with or without His6, FIG. 6B, lanes 4 and 5) when the cells are coinfected with the two types of recombinant virus but not when only one of the proteins is expressed (corresponding lanes 1,2 and 3). Conversely, in the anti-APP immunoprecipitates, the PS1-His6 proteins and PS1 are detectable (FIG. 6C, lanes 4 and 5) for the double infections. This experiment allows the interaction in the reverse sense with different antibodies to be confirmed.

Example 4

Interaction of Aβ and PS2 in Cells

Given that the region of interaction between the APP and the PS2 involves on the APP, a region including the amyloid peptide (from 595 to 635) and on the PS2, its hydrophilic N-term domain, it is demonstrated in this example that the latter interacts directly with the amyloid peptide (Aβ) produced by cells. The expression of SPA4CT (corresponding to the 100 last residues of the APP preceded by a signal peptide) in COS cells leads to a high production of the amyloid peptide, in part because SPA4CT is considered as the biological precursor of the Aβ. The COS cells were transfected with SPA4CT alone, SPA4CT and SecPS2Nt or with SecPS2Nt alone. The corresponding extracellular media were immunoprecipitated with the anti-PS2 antibody and the Aβ peptide was detected with the aid of the specific antibody W02 (Nida et al., (1996) J. Biol. Chem. 271, 22908–914) (FIG. 7). The Aβ peptide is identified only for the cells cotransfected with SecPS2Nt and SPA4CT as a band of weak intensity (FIG. 7, lane 1) but not with the individual controls (lanes 2 and 3). Moreover, an additional band at approximately 40 kDa is also detected specifically for the doubly transfected cells. After washing of the filter and detection with the PS2 antibody, it appears that a band at the same molecular weight is likewise PS2-immunoreactive (FIG. 7, lane 4). This band is also present for the cells transfected with SecPS2Nt as expected. Thus, in the doubly transfected cells, this band represents an SDS-stable complex between SecPS2Nt and the Aβ, able to confirm the interaction between these two entities. The slight difference in mass contributed by the Aβ peptide (4 kDa) will explain that there was no size difference detectable with the cells transfected with SecPS2Nt alone. The results of these experiments allow it to be concluded that the secreted form of PS2 (secPS2Nt) interacts in vitro with the peptide Aβ (residues 597–637 of APP695).

Example 5

Reconstitution of the Interaction of Aβ and PS2Nt in an in Vitro Test on Nitrocellulose Membranes This example has the aim of demonstrating the reconstitution of the PS2Nt-APP(Aβ) interaction in vitro.

To confirm the interaction between the Aβ peptide and PS2Nt (N-terminal end of PS2), an in vitro immobilization test was developed. A PS2Nt fusion protein carrying the S marker/label peptide (S-tag) at its N-terminal end was constructed and expressed in bacterium. The peptides $Aβ_{1-40}$ and $Aβ_{1-42}$ were deposited on nitrocellulose membranes which were incubated in the presence of a bacterial extract expressing the protein PS2Nt. The S-tag was then visualized with the S-tag immobilizing protein coupled to the alkaline phosphatase and by calorimetric reaction. The S-tag-PS2Nt protein is immobilized well on the Aβ peptides in this in vitro test (FIG. 8A). As controls, duplicates were incubated in the presence of a bacterial extract only expressing the S peptide which is used as a non-specific immobilization level on the Aβ peptide (forms 1-40 and 1-42). Serial dilutions of the bacterial extract allow it to be established that this immobilization is dose-dependent and saturable. In this experiment, the immobilization seems to be more important on the $Aβ_{1-42}$ than on the $Aβ_{1-40}$ with, however, a certain variability. For example, the immobilization of PS2Nt is dependent on the dose of Aβ deposited on the membrane, although $Aβ_{1-40}$ and $Aβ_{1-42}$ show equivalent immobilization values.

This example thus supplies a demonstration of the reconstitution of the in vitro PS2Nt-App(Aβ) interaction between synthetic Aβ and PS2NT of bacterial origin. Given that the pathological mutations of PS2 lead to an increase in the Aβ1-42/Aβ1-40 ratio produced in numerous systems and that, moreover, there is physical interaction between PS2 and APP, it appears that this physical interaction could be involved in the production of the $Aβ_{1-42}$ peptide. Thus, the inhibition of this interaction forms an extremely original therapeutic approach for Alzheimer's disease.

Example 6

Aβ42/PS2NT Interaction Test in 96-well Format (ELISA type). FIG. 11

Example 5 supplies results demonstrating the direct interaction between the Aβ peptide and the PS2NT protein on nitrocellulose membrane. This example has the aim of confirming the information in Example 5 and of describing the demonstration of the interaction in a 96-well plate format. The Aβ peptide (Aβ40 or Aβ42) is immobilized by incubation on plastic 96-well plates. The plates are then incubated with the recombinant PS2NT protein. After rinsing, the detection of the interaction (Aβ/PS2NT) is carried out by immobilization of the immobilizing protein of the S-tag in the wells and calorimetric visualization. PS2NT is immobilized in a dose-dependent fashion on the Aβ1-42 peptide (FIG. 11) but not on the Aβ1-40 peptide or on the inverted sequence peptide Aβ40-1, nor on another amyloidogenous peptide, amyline. The quantities of Aβ1-42 or Aβ1-40 peptides immobilized on the plates are identical as verified by immunodetection). The immobilization constant of PS2NT on Aβ42 is 0.18 μM. The specificity of PS2NT for the Aβ42 form of the peptide with respect to Aβ40 had only been suggested in Example 5. This example establishes this specificity which is perfectly reproducible in the present test.

This format of Aβ42/PS2NT interaction test thus allows a screening test for molecules which inhibit this interaction to be easily envisaged.

Example 7

Aβ42/PS2NT Interaction Test in HTRF Format

In Examples 5 and 6, the direct interaction between the Aβ42 peptide and the PS2NT protein has been demonstrated on the one hand on nitrocellulose membrane and on the other hand by 96-well plates (ELISA type).

This example has the aim of confirming this information and it describes the demonstration of the interaction in liquid/homogeneous phase by using the fluorescence transfer technique.

The principle of the test described in Materials and Methods (5.4) is based on fluorescence transfer. The recombinant protein PS2NT labelled with europium cryptate (PS2NT-K) interacts with the biot-Aβ42 peptide as FIG. 12 shows (bar No. 3). This signal is decreased and thus the PS2NT-K/biot-Aβ42 interaction is displaced by an excess of unlabelled PS2NT (C150=400 nM). The detected fluorescence signal is stable over time: from 4 h at ambient temperature to 24 h at 4° C. (according to the conditions chosen, described in Materials and Methods).

This interaction is dose-dependent for the biot-Aβ42 peptide (zone of linearity of the signal from 0 to 2.5 μM) and for PS2NT-K (zone of linearity of the signal from 0 to 7.5 nM). As indicated in FIG. 12, bar No. 5, there is no interaction of PS2NT-K with the biot-Aβ40 peptide supplying a supplementary element of specificity. The specificity of PS2NT for the Aβ42 form of the peptide with respect to Aβ40 which had only been suggested in Example 5 is thus confirmed in Example 6 and the present example.

This HTRF interaction test between PS2NT and Aβ42 (reflecting the APP/PS interaction in cells) thus allows the identification of chemical molecules inhibiting this interaction by high flow screening.

Example 8

Reconstitution of the APP/PS1 Interaction in Vitro

This example has the aim of demonstrating that the interaction between the complete APP and PS1 proteins can be recreated from different cell lysates, mixed solely to demonstrate the interaction.

The baculovirus expression system allowing the expression of large quantities of recombinant proteins, the lysates of cells infected individually by each of the three viruses were used as source of APP, PS1 and PS1-His6 proteins. The solubilized fractions containing the APP, PS1 or 6HisPS1 are mixed, then immunoprecipitated in the presence of antihistidine or antiPS1 antibodies for one night at 4° C. The APP is clearly detected in the immunoprecipitates (FIG. 9A, lane 3 and FIG. 9B, lane 3) demonstrating that the APP interaction with PS1-His or PS1 is reconstituted in vitro by incubation of the two proteins. The APP alone seems to be slightly precipitated by the anti-PS1 antibody (FIG. 9B, lane 1) but not with the anti-His antibody, confirming the specificity of the interaction in this case. These results allow the perfection of an in-vitro interaction test of the two complete proteins APP and PS1.

Example 9

SecPS2Nt Blocks the Interaction of APP and PS1 in Transfected Cells

It was demonstrated in the preceding examples that APP interacts with PS1 in a similar manner to PS2 and that for the latter, the construct SecPS2Nt suffices in the interaction with APP. This example has the aim of evaluating if the immobilization of SecPS2Nt on the APP can block the interaction with PS1 in an overlapping (heterologous) manner. In the COS1 system, the SPA4CT (corresponding to the last 100 residues of the APP preceded by a signal peptide) can be detected in the anti-PS1 immunoprecipitates of the cells expressing SPA4CT and PS1 wt or mutant PS1, PS1*, (FIG. 10A, lanes 1 and 2). Furthermore, when SecPS2NT is also cotransfected, the SPA4CT signal almost disappears in the anti-PS1 immunoprecipitates (FIG. 10A, lanes 3 and 4). After the anti-PS1 immunoprecipitation, the supernatants (fraction not bound to protein A sepharose) underwent a second immunoprecipitation with the anti-PS2 antibody. The SPA4CT is clearly detected in the cells cotransfected with PS1 and SecPS2Nt (FIG. 10B, lanes 3 and 4) demonstrating that in these cells, SecPS2Nt in being immobilized has displaced the immobilization of SPA4CT on PS1. This experiment thus allows it to be concluded that SecPS2Nt is a molecule capable not only of being immobilized on APP, but also of displacing the immobilization of APP on PS1 and probably PS2. SecPS2Nt can thus serve in cells as a trap to block the APP interaction with the two presenilins, PS1 and PS2. In fact, the results of the mapping of the PS1/APP interaction confirm that the interaction zones involved are similar to those of PS2.

Example 10

The blocking of the APP/PS1 Interaction Leads to the Inhibition of the Production of the Intracellular A β42 Amyloid Peptide The preceding example demonstrates that the expression of SecPS2NT can block the interaction between APP and PS1 or mutant PS1. The present example analyses the consequences of this inhibition on the production of the amyloid peptide, in particular of these two forms Aβ40 and Aβ42. In fact, it has been described above in the literature that the pathological mutations of the presenilins (PS1 or PS2) led to an increase in the ratio of the long form of the Aβ peptide, Aβ42 form, over the Aβ40 form, Aβ42/Aβ40 ratio (Borchelt et al. 1996 and for revue Hardy, 1997).

Figure 13B:
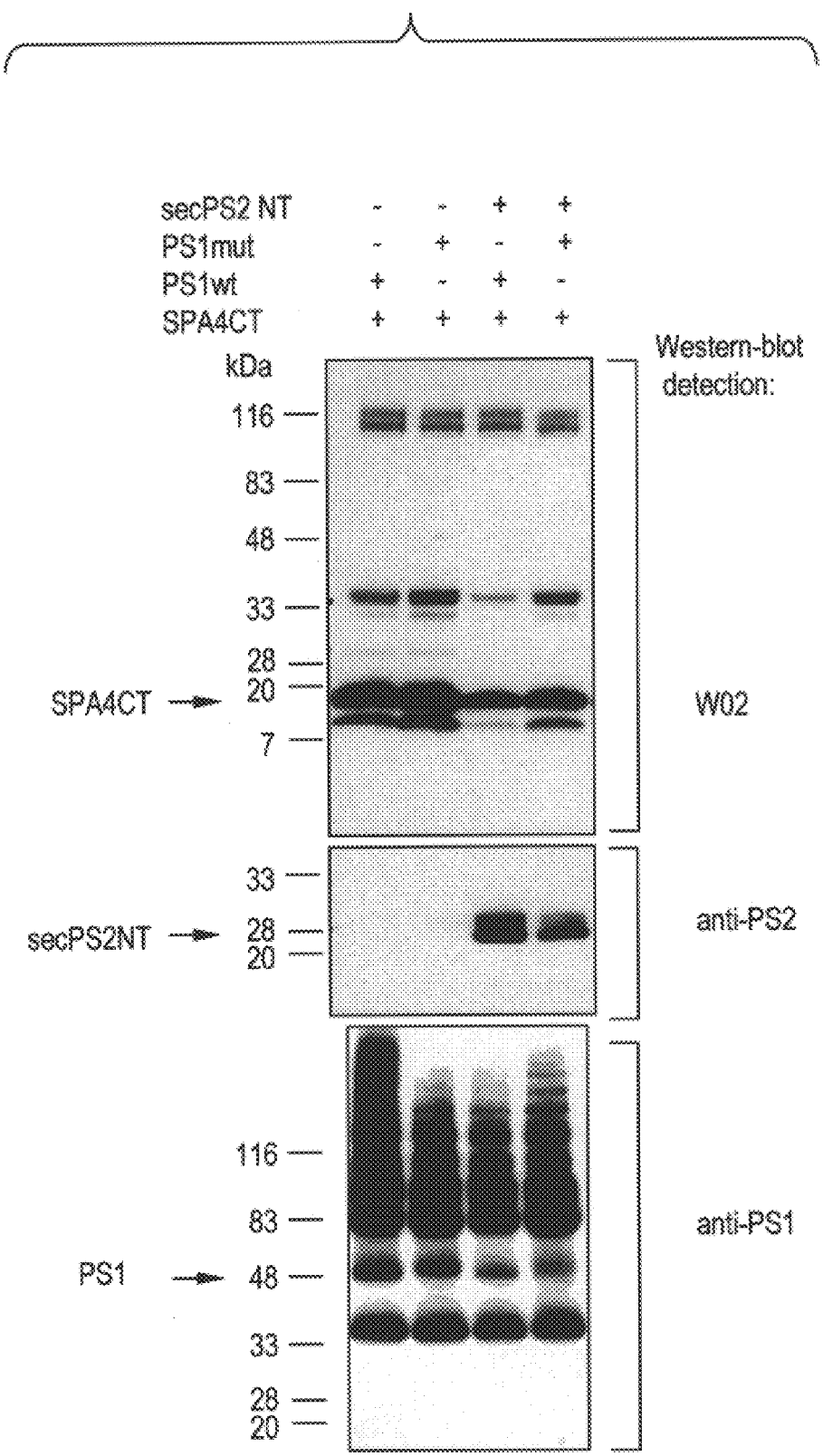

SPA4CT was coexpressed with PS1 wt (FIG. 13 A, lanes 1 & 3) or with mutant PS1 (FIG. 13 A, lanes 2 & 4) either in the absence (lanes 1 & 2) or in the presence of SecPS2NT (lanes 3 & 4). The cell lysates and the conditioned media of the cells were analysed for the production of the amyloid peptide. The Aβ40 and Aβ42 forms were analysed by immunoprecipitation with antibodies specifically recognizing the Aβ40 (FCA3340) or Aβ42 (FCA3542, Barelli et al., 1997) C-terminal ends and the immunoprecipitates were analysed by immunoblot with an antibody recognizing the two forms. In the cell lysates, the expression of mutant PS1 indeed leads to an increase in the production of Aβ42 (1.5 to 2 times) and of its multimeric forms with respect to PS1wt and little variation of the levels of Aβ40 (compare FIG. 13 A, lanes 1 and 2, Aβ42 and Aβ40 cell lysate panels) as expected. In the presence of SecPS2NT, the levels of Aβ42 (and multimers) are considerably reduced (FIG. 13 A, lanes 3 and 4) as much with PS1 wt as with mutant PS1. In the extracellular medium, the levels of Aβ42 also seem to be decreased but less significantly. There is no variation of the levels of amyloid peptide Aβ40 between the different conditions, which demonstrates that the effect on Aβ42 is specific and is not due to a global modification of the expression levels. This is confirmed by the analysis of the expression of the different transfected genes: SPA4CT, SecPS2NT and PS1 (FIG. 13B). In this example, it has thus been demonstrated that inhibition of the PS1/APP interaction with the genetic dominant SecPS2NT leads to a decrease in the levels of production of intracellular Aβ42 as much with mutant PS1 as with PS1 wt. With regard to the essential role granted to Aβ42 in the development of Alzheimer's disease, this example demonstrates that the inhibition of the APP/PS interaction thus represents a significant therapeutic target as much for the genetic forms as the sporadic forms of the disease.

Example 11

Detection of the Interaction of PS2 With the Endogenous APP of COS Cells With the aid of Pharmacological Treatment This example has the aim of demonstrating that the results obtained in the preceding examples (these results in cells, corresponded to the overexpression of the two partners of the APP and PS (PS1 or PS2) interaction) are equally valid with non-overexpressed or endogenous proteins. In fact, the strong overexpression of the two proteins could lead to an interaction artefact. The detection of the interaction under conditions not involving the simultaneous overexpression of the two partners was investigated in this example.

The COS cells express the APP endogenously as well as at low levels. The COS cells were thus transfected with PS2 only. The cell lysates were analysed by immunoprecipitation with the antibody directed against the peptide of the N-term of PS2 and visualized by immunoblotting with the anti-APP, WO2 antibody. The upper panel of FIG. 14 shows that the transfection with PS2 alone does not allow interaction with endogenous APP to be detected by co-immunoprecipitation (FIG. 14, lane 1).

In addition, since the APP/PS interaction leads to the production of the amyloid peptide Aβ42 (preceding example), thus to the catabolism of the APP, at the level of the endoplasmic reticulum, the proteasome which is the proteolytic degradation system in this cell compartment could be involved. The effect of lactacystine, a selective inhibitor of the proteasome was analysed. After incubation of cells transfected with PS2 in the presence of lactacystine, the endogenous APP of the COS cells can be clearly demonstrated in the PS2 immunoprecipitates (FIG. 14, lane 5, band at 110 kDa). This interaction with the endogenous APP has the same characteristics as above since it can be displaced by the genetic dominant SecPS2NT (FIG. 14, lanes 6 and 7) with a dose-dependent effect. In fact, lane 7 shows that at a moderate dose of SecPS2NT, a band of weak intensity corresponding to the endogenous APP is always visible. At a more significant dose of SecPS2NT (lane 6), the band corresponding to the endogenous APP appears very weakly and demonstrates the dose-dependent character. A weak residual APP signal is always present (band at approximately 110 kDa) and is due to the complex between APP and SecPS2NT which is rapidly secreted (since SecPS2Nt does not have any more transmembrane anchoring domains) and thus does not accumulate intracellularly.

Figure 14:
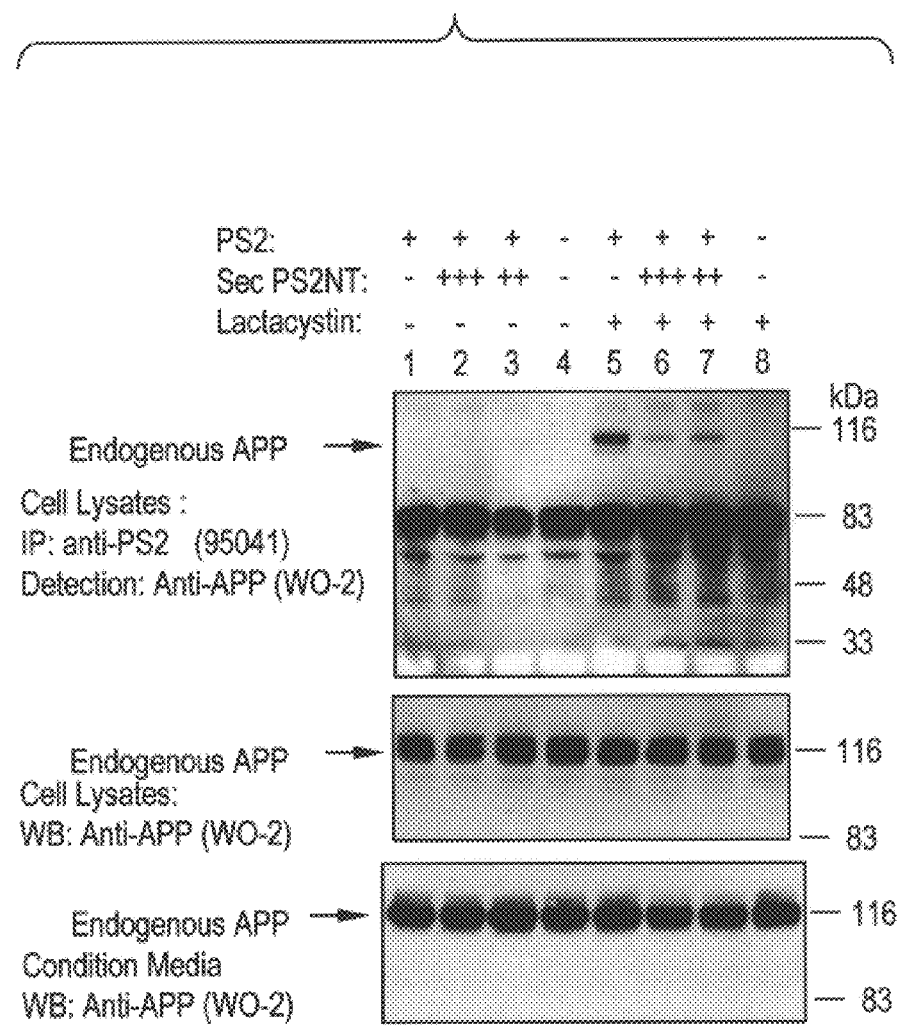

FIG. 14 (middle and lower panels) shows that treatment with lactacystine does not affect the total levels of APP, either cellular or secreted. In fact, the bands corresponding to the levels of expression of APP are almost constant in intensity. The specificity of the lactacystine effect is thus demonstrated on the sub-population of APP in interaction with PS2.

By these results, it could be demonstrated that the APP/PS2 interaction can be detected with endogenous APP of COS cells if the proteasome is inhibited. In addition, these results demonstrate that the APP/PS2 interaction can be detected under less artificial conditions. However, this interaction is very labile. In addition, in order to obtain a more marked detection, recourse has been made either to an inhibitor of proteolytic degradation in the present example or to the overexpression of the two partners in the preceding examples. This example thus demonstrates that the results obtained in the preceding examples with overexpression in the cell of the two partners of the interaction (APP and PS1 or PS2) are equally valid with non-overexpressed or endogenous proteins.

Example 12

PS2 Interacts With a Second Segment of APP, Other Than Aβ

This example aims to demonstrate that another segment of APP interacts with PS2.

Figure 15:
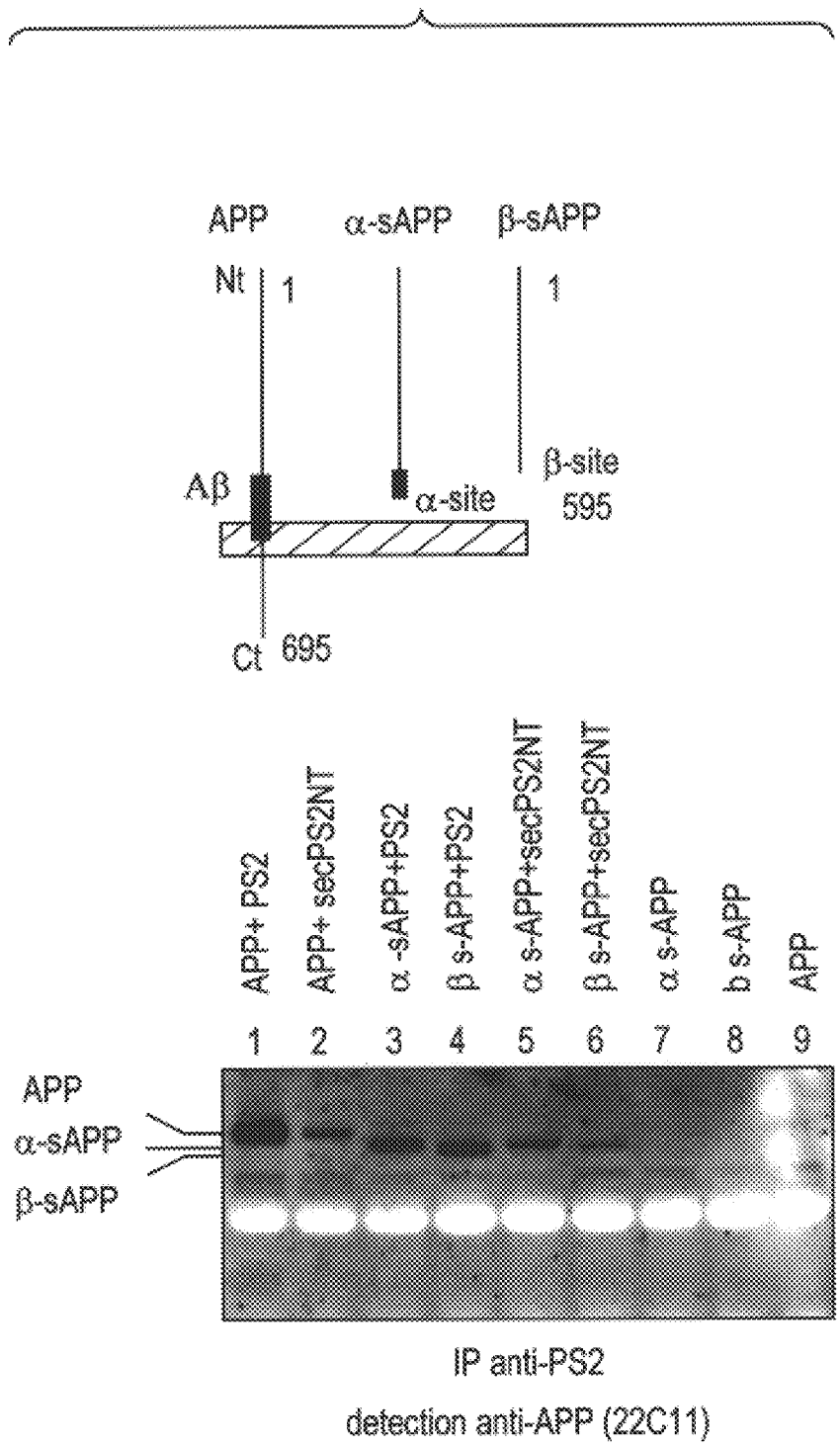

It was previously demonstrated that SecPS2NT interacts in the extracellular medium with the secreted forms of APP (FIG. 3A, lane 4). The secreted forms of the APP are liberated after cleavage either at the β site (position 595), corresponding to the start of the Aβ peptide, or at the α site (position 612) at the very midst of this peptide. These results suggest that PS2NT also interacts with an N-term region of APP different from Aβ. Truncated forms of APP were constructed, by insertion of a stop codon in the β (β-sAPP) and α (α-sAPP) sites and were tested. Complete PS2 and SecPS2NT interact effectively with α-sAPP (FIG. 15, lanes 3 and 5) and β-sAPP (FIG. 15, lanes 4 and 6). These results establish that a segment of APP comprised between position 1 and 595 (and thus other than Aβ) is likewise capable of interacting with PS2 and PS2NT. These results additionally allow it to be confirmed that the PS2NT/APP interaction can take place in the absence of anchorage to the membrane of the two partners and in the luminal (or extracellular) compartment of the cell.

References

Doan et al. (1996) Protein topology of presenilin1. Neuron 17:1023–1030.

Thinakaran et al., (1996) Endoproteolysis of Presenilin1 and accumulation of processed derivatives in vivo. Neuron 17:181–190.

Podlisny et al., (1997) Presenilin proteins undergo heterogeneous endoproteolysis between Thr291 and Ala299 and occur as stable N- and C-terminal fragments in normal and Alzheimer brain tissue. Neurobiology of Disease 3:325–337.

Pradier, L., Czech, C., Mercken, L., Revah, F. and Imperato, A. (1996) Biochemical characterization of presenilins (S182 and STM2) proteins. Neurobiol. Aging 17:S137

Scheuner et al. (1996) Secreted amyloid β-protein similar to that in the senile plaques of Alzheimer's disease is increased in vivo by the presenilin 1 and 2 and APP mutations linked to familial Alzheimer's disease. Nature Med. 2: 864–870.

Dyrks, T., Dyrks, E., Mönning, U., Urmoneit, B., Turner, J. and Beyreuther, K. (1993) Generation of βA4 from the amyloid protein precursor and fragment thereof. FEBS Lett. 335:89–93.

Weidemann, A., Paliga, K., Düirrwang, U., Czech, C., Evin, G., Masters, C., & Beyreuther, K. (1997). Formation of stable complexes between two Alzheimer's disease gene products: Presenilin-2 and β-Amyloid precursor protein. Nature Medicine 3:328–332.

Blanchard, V., Czech, C., Bonici, B., Clavel, N., Gohin, M., Dalet, K., Revah, F., Pradier, L., Imperato, A. and S. Moussaoui. (1997) Immunohistochemical analysis of presenilin 2 expression in the mouse brain: distribution pattern and co-localization with presenilin 1 protein. Brain Res. 758:209–217.

Borchelt, D. R., Thinakaran, G., Eckman, C., Lee, M. K., Davenport, F., Ratovitsky, T., Prada, C.-M., Kim, G., Seekins, S., Yager, D., Slunt, H. H., Wang, R., Seeger, M., Levey, A. I., Gandy, S. E., Copeland, N. G., Jenkins, N., Price, D. L., Younkin, S. G. and S. Sisodia (1996) Familial Alzheimer's disease-linked presenilin 1 variants elevate Aβ1-42/1-40 ratio in vitro and in vivo. Neuron 17:1005–1013

Duff, K., Eckman, C., Zehr, C., Yu, X., Prada, C.-M., Perez-tur, J., Hutton, M., Buee, L; Harigaya, Y., Yager, D., Morgan, D., Gordon, M. N., Holcomb, L., Refolo, L., Zenk, B., Hardy, J. and S. Younkin (1996) Increased amyloid-β42(43) in brains of mice expressing mutant presenilin1. Nature 383:710–713.

Hardy, J. (1997) Amyloid, the presenilins and Alzheimer's disease. Trends in Neurosci. 20:154–159.

Stephens, D. J. and B. M. Austen (1996) Metabolites of the β-amyloid precursor protein generated by β-secretase localise to the Trans-Golgi Network and late endosome in 293 cells. J. Neurosci. Res 46:211–225.

Essalmani, R., Guillaume, J.-M., Mercken, L., and Octave, J.-N. (1996). Baculovirus-Infected Cells Do not Produce the Amyloid Peptide of Alzheimer's Disease from its Precursor. FEBS Lett. 389:157–161.

Barelli et al., (1997), Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases. Molecular medecine 3:695–707.

What is claimed is:

1. A process for determining whether a compound or ligand has the ability to inhibit the formation of a complex between an N-terminal end of Presenilin 2 and a β-amyloid peptide$_{1-42}$ (Aβ$_{1-42}$), wherein the process comprises:

(a) contacting a detectably labeled N-terminal end of Presenilin 2 and the compound with the Aβ$_{1-42}$; and (b) detecting inhibition of the formation of a complex between the N-terminal end Presenilin 2 and the Aβ$_{1-42}$.

2. The process of claim 1, further comprising isolating the compound or ligand.

3. The process of claim 2, wherein the isolated compound or ligand is capable of inhibiting at least in part the formation of a complex between Aβ$_{1-42}$ the N-terminal end of the Presenilin 2.

4. The process according to claim 1, wherein the Aβ$_{1-42}$ comprises a biotin and an arm of 3 β-alanines or 3 lysines at its N-terminal end, and the process comprises the steps of forming a mixture of the compound or ligand with the Aβ$_{1-42}$, incubating the mixture with an N-terminal end of Presenilin 2 that is labeled with a first fluorophore, adding a streptavidin coupled to a second fluorophore wherein the second fluorophore is capable of being excited at an emission wavelength of the first fluorophore, and detecting the inhibition of the interaction between the Aβ$_{1-42}$ and the purified Presenilin 2 by spectrofluorometry at the emission wavelength of the first fluorophore, at the emission wavelength of the second fluorophore, or at the emission wavelengths of the first and second fluorophores.

5. The process according to claim 4, wherein the first fluorophore is europium cryptate and the second fluorophore is XL665.

6. The process according to claim 5, wherein the emission wavelength of the first fluorophore is 620 nm and the emission wavelength of the second fluorophore is 665 nm.

* * * * *